(12) United States Patent
Dillon et al.

(10) Patent No.: US 6,979,696 B2
(45) Date of Patent: Dec. 27, 2005

(54) METHOD FOR DETECTING A GRAM-NEGATIVE BACTERIAL AUTOINDUCER MOLECULE

(75) Inventors: Michael Patrick Dillon, San Carlos, CA (US); Clara Jeou Jen Lin, Palo Alto, CA (US); Amy Geraldine Moore, Mountain View, CA (US); Counde O'Yang, Sunnyvale, CA (US); Yansheng Zhai, East Palo Alto, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 38 days.

(21) Appl. No.: 10/841,288

(22) Filed: May 7, 2004

(65) Prior Publication Data

US 2004/0224973 A1 Nov. 11, 2004

Related U.S. Application Data

(60) Provisional application No. 60/469,255, filed on May 9, 2003.

(51) Int. Cl.⁷ .................. A61K 31/415; C07D 233/64
(52) U.S. Cl. ............... 514/398; 514/399; 514/400; 548/339.5; 548/340.1; 548/341.1; 548/341.5; 548/342.1; 548/300.1
(58) Field of Search ............... 514/398, 399, 514/400; 548/300.1, 339.5, 340.1, 341.1, 341.5, 342.1

(56) References Cited

U.S. PATENT DOCUMENTS

| | | |
|---|---|---|
| 3,491,114 A | 1/1970 | Suh |
| 3,586,695 A * | 6/1971 | Wysong et al. .......... 548/312.1 |
| 5,952,362 A * | 9/1999 | Cournoyer et al. .......... 514/398 |

FOREIGN PATENT DOCUMENTS

| | | |
|---|---|---|
| EP | 0 458 207 B1 | 3/1997 |
| WO | WO 94/29290 A1 | 12/1994 |
| WO | WO 98/21184 A1 | 5/1998 |
| WO | WO 01/70687 A1 | 9/2001 |

* cited by examiner

*Primary Examiner*—Joseph K. McKane
*Assistant Examiner*—Susannah E. Lee
(74) *Attorney, Agent, or Firm*—Robert C. Hall

(57) ABSTRACT

This invention relates to compounds which are alpha-1 receptor agonists, preferably alpha-1A/L receptor agonists, and which are represented by Formula I:

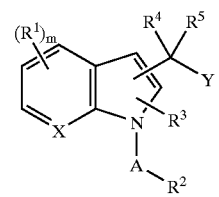

wherein m, A, X, Y, $R^1$, $R^2$, $R^3$, $R^4$ and $R^5$ are as defined in the specification; or individual isomers, racemic or non-racemic mixtures of isomers, or pharmaceutically acceptable salts or solvates thereof. The invention further relates to pharmaceutical compositions containing such compounds, methods for their use as therapeutic agents, and methods of preparation thereof.

56 Claims, No Drawings

METHOD FOR DETECTING A GRAM-NEGATIVE BACTERIAL AUTOINDUCER MOLECULE

CROSS REFERENCE TO PRIOR APPLICATION

This application claims benefit under Title 35 U.S.C. 119(e) of U.S. Provisional Application No. 60/469,255, filed May 9, 2003, which is hereby incorporated by reference in its entirety.

FIELD OF THE INVENTION

This invention relates to substituted indoles which are alpha-1 adrenergic agonists, preferably alpha-1A/L adrenergic agonists, and associated pharmaceutical compositions, methods for use as therapeutic agents, and methods of preparation thereof.

BACKGROUND OF THE INVENTION

Alpha-1 adrenergic receptors (interchangeably named alpha-1 adrenoceptors) are G-protein coupled transmembrane receptors that mediate various actions of the sympathetic nervous system through the binding of the catecholamines, epinephrine and norepinephrine (NE). Currently, several subtypes of the alpha-1 adrenergic receptors are known to exist for which the genes have been cloned: alpha-1A (previously known as alpha-1C), alpha-1B and alpha-1D. Recently the existence of a low affinity alpha-1 adrenoceptor for prazosin named alpha-1L, in human prostate has been determined. However, the gene for the alpha-1L adrenergic receptor subtype has yet to be cloned. The alpha-1 adrenoceptor plays a part in the sympathetic maintenance of smooth muscle tone and alpha-1 adrenergic agonists are known to increase muscle tone in the lower urinary tract necessary for urine storage and urine emptying thus making adrenergic receptors important targets for drug development in urinary dysfunction (Testa, R., *Eur. J. Pharmacol.*, 1993, 249, 307–315. Pharmacological studies resulting in the subdivision of alpha-1 adrenergic receptors have let to the suggestion that development of subtype-selective compounds may allow improved treatment with a lower incidence of side effects, and Tanaguchi et al., *Eur. J. Pharmacol*, 1996, 318, 117–122, have reported that compounds with selectivity for the alpha-1A receptor and to a lessen extent to the alpha-1L receptor over the alpha-1B and alpha-1D subtypes have selectivity for urethral over vascular tissue.

Certain alpha-1A agonists are known and are indicated to be useful in treating various disease states including urinary incontinence, nasal congestion, sexual dysfunction such as ejaculation disorders and priapism, and CNS disorders such as depression, anxiety, dementia, senility, Alzheimer's, deficiencies in attentiveness and cognition, and eating disorders such as obesity, bulimia, and anorexia, see for example U.S. Pat. No. 5,952,362 (Cournoyer et al.) which discloses a variety of alpha-1A/L agonists including some 2-imidazoline, 2-oxazoline, 2-hiazoline and 4-imidazole derivatives.

Urinary incontinence is a condition defined as the involuntary loss of urine to such an extent as to become a hygienic or social concern to the patient. Stress urinary incontinence (SUI) occurs when the internal sphincter does not close completely. The primary symptom is minor leakage from activities, such as coughing, sneezing, laughing, running, lifting, or even standing, that apply pressure to a full bladder. Leakage stops when the activity stops. SUI is most common in women between the ages of 25 and 50, and many regularly exercising women have some degree of SUI.

The methods presently available to treat SUI include physiotherapy and surgery. Treatment with pharmaceuticals is limited to the use of non-selective adrenergic agonists. Only a limited number of pharmaceutical agents have been employed, with varying success, to treat stress incontinence.

Phenylpropanolamine, pseudoephrine and midodrine are considered first-line therapy for mild to moderate stress incontinence (Wein, supra; Lundberg (editor), *JAMA* 1989, 261(18):2685–2690). These agents are believed to work both by direct activation of alpha-1 adrenoceptors and indirectly by displacement of endogenous norepinephrine from sympathetic neurons following uptake into the nerve terminal (Andersson and Siogren, *Progress in Neurobiology*, 1982, 71–89). Activation of alpha-1 adrenoceptors located on the smooth muscle cells of the proximal urethra and bladder neck (Sourander, *Gerontology* 1990, 36:19–26; Wein, supra) evokes contraction and an increase in urethral closure pressure.

The utility of phenylpropanolamine, pseudoephrine, and midodrine is limited by a lack of selectivity among the alpha-1 adrenoceptor subtypes and by the indirect action of these agents (i.e. activation of alpha-1, alpha-2, and beta-adrenoceptors in the central nervous system and periphery). As a result, any desired therapeutic effect of these agents may be accompanied by undesirable side effects such as an increase in blood pressure. The increase in blood pressure is dose-dependent and therefore limits the ability to achieve therapeutically effective circulating concentrations of these agents (Andersson and Sjogren, supra). Furthermore, in some patients these agents produce insomnia, anxiety and dizziness as a result of their central nervous system stimulant actions (Andersson and Sjogren, supra, Wein, supra).

Due to side effects and/or limited efficacy associated with the current available medicaments, there is an unmet medical need for useful compounds. A compound having the desired alpha-1A/L adrenergic agonist profile is desirable.

SUMMARY OF THE INVENTION

The invention provides compounds of the formula I:

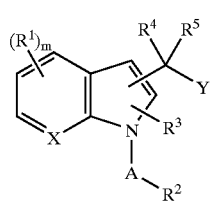

I and pharmaceutically acceptable salts and prodrugs thereof, wherein:

m is from 0 to 4;

X is carbon or nitrogen;

Y is a radical of formula i, ii or iii;

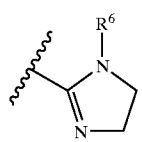

i

-continued

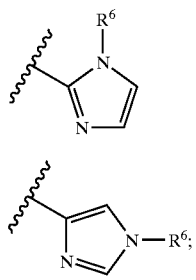

ii iii each $R^1$ independently is halogen, haloalkyl, alkyl, hydroxy, alkoxy, cyano, nitro, —S(O)$_n$R$^a$, —NR$^a$R$^b$, —NR$^a$SO$_2$R$^b$, —SO$_2$NR$^a$R$^b$, optionally substituted phenyl, optionally substituted benzyl or optionally substituted benzyloxy, where n is from 0 to 2 and R$^a$ and R$^b$ in each independent occurrence is hydrogen or alkyl;

A is —SO$_2$— or —(C=O)—;

$R^2$ is alkyl or —(CH$_2$)$_p$—NR$^c$R$^d$ where p is from 0 to 3 and R$^c$ and R$^d$ each independently is hydrogen or alkyl; and $R^3$, $R^4$, $R^5$ and $R^6$ each independently is hydrogen or alkyl.

Those skilled in the art will recognize that stereoisomers exist in some compounds of formula I. Accordingly, the present invention includes all possible stereoisomers, and geometric isomers and includes not only racemic compounds but also the optically active compounds as well. Additionally when tautomers of the compounds of formula I are possible, the present invention is intended to include all tautomeric forms of the compounds.

The invention further relates to pharmaceutical compositions containing a therapeutically effective amount of at least one compound of formula I, or individual isomers, racemic or non-racemic mixtures of isomers, or pharmaceutically acceptable salts or solvates thereof, in admixture with at least one suitable carrier.

In another embodiment the method of treating a subject comprises administering to a subject having a disease state which is alleviated by treatment with an alpha-1A/L receptor agonist, a therapeutically effective amount of one or more compounds of formula I.

In another embodiment, the method of treating a subject comprises administering to a subject having a disease state which is alleviated by treatment with an alpha-1A/L receptor agonist, a pharmaceutically effective amount of the pharmaceutical composition containing at least one compound of formula I. The disease state may comprise urinary incontinence, nasal congestion, sexual dysfunction such as ejaculation disorders and priapism, and central nervous system (CNS) disorders such as depression, anxiety, dementia, senility, Alzheimer's, deficiencies in attentiveness and cognition, and eating disorders such as obesity, bulimia, and anorexia.

In another embodiment the disease state may be selected from urge incontinence, stress incontinence, overflow incontinence and functional incontinence.

In another embodiment the disease may comprise nasal congestion associated with allergies, colds, and other nasal disorders, as well as the sequelae of congestion of the mucous membranes (for example, sinusitis and otitis media). Another aspect of this invention involves methods for preventing or treating nasal congestion by administering a safe and effective amount of a subject compound to a mammal experiencing or at risk of experiencing nasal congestion. Such nasal congestion may be associated with human diseases or disorders which include, but are not limited to, seasonal allergic rhinitis, acute upper respiratory viral infections, sinusitis, perennial rhinitis, and vasomotor rhinitis. In addition, other disorders can be generally associated with mucous membrane congestion (for example, otitis media and sinusitis).

In still another preferred embodiment, the invention provides a process which comprises reacting a compound of the formula v:

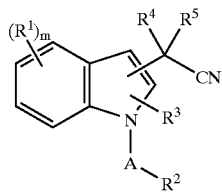

v wherein m, A, $R^1$, $R^2$ and $R^3$ are as defined herein, with an alkylene diamine compound to form a compound of the formula I:

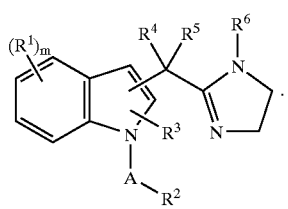

I

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear, branched or cyclic saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, cyclopropyl, isopropyl, isobutyl, sec-butyl, tert-butyl, pentyl, n-hexyl, octyl, dodecyl, and the like.

"Lower alkyl" means the monovalent linear or branched saturated hydrocarbon radical, consisting solely of carbon and hydrogen atoms, having from one to six carbon atoms inclusive, unless otherwise indicated. Examples of lower alkyl radicals include, but are not limited to, methyl, ethyl, n-propyl, isopropyl, sec-butyl, tert-butyl, n-butyl, n-pentyl, n-hexyl, and the like.

"Alkylene" means a linear saturated divalent hydrocarbon radical of one to six carbon atoms or a branched saturated divalent hydrocarbon radical of three to six carbon atoms. $C_2$–$C_3$ alkylenes include, by way of example, methylene, ethylene, 2,2-dimethylethylene, propylene, 2-methylpropylene, and the like.

"Alkoxy" means the radical —O—R, wherein R is a lower alkyl radical as defined herein. Examples of alkoxy radicals include, but are not limited to, methoxy, ethoxy, isopropoxy, isobutoxy and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, allyl and the like.

"Aryl" means the monovalent cyclic aromatic hydrocarbon radical consisting of one or more fused rings in which at least one ring is aromatic in nature, which can optionally be substituted with hydroxy, cyano, lower alkyl, lower alkoxy, alkylthio, halo, haloalkyl, hydroxyalkyl, nitro, alkoxycarbonyl, amino, alkylamino, dialkylamino, aminocarbonyl, carbonylamino, aminosulfonyl, sulfonylamino, nitro, and/or alkylsulphonyl, unless otherwise indicated. Examples of aryl radicals include, but are not limited to, phenyl, naphthyl, biphenyl, indanyl, anthraquinolyl, and the like.

"Heteroaryl" means the monovalent aromatic carbocyclic radical having one or more rings incorporating one, two, or three heteroatoms within the ring (chosen from nitrogen, oxygen, or sulfur) which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or alkylsulfonyl, unless otherwise indicated. Examples of heteroaryl radicals include, but are not limited to, imidazolyl, oxazolyl, thiazolyl, pyrazinyl, thiophenyl, furanyl, pyranyl, pyridinyl, quinolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, quinolinyl, isoquinolinyl, quinuclidinyl, naphtyridinyl, and the like.

"Arylsulfonyl" means a radical —S(O)$_2$R where R is an aryl group as defined herein.

"Cycloalkyl" means a saturated monovalent cyclic hydrocarbon radical of three to seven ring carbons. The cycloalkyl may be optionally substituted independently with one, two, or three substituents selected from alkyl, optionally substituted phenyl, or —C(O)R (where R is hydrogen, alkyl, haloalkyl, amino, acylamino, mono-alkylamino, di-alkylamino, hydroxy, alkoxy, or optionally substituted phenyl). More specifically, the term cycloalkyl includes, for example, cyclopropyl, cyclohexyl, phenylcyclohexyl, 4-carboxycyclohexyl, 2-carboxamidocyclohexyl, 2-dimethylaminocarbonyl-cyclohexyl, and the like.

"Cycloalkylalkyl" means a radical —R$^a$R$^b$ where R$^a$ is an alkylene group and R$^b$ is a cycloalkyl group as defined herein, e.g., cyclopropylmethyl, cyclopropylethyl, cyclobutylmethyl, cyclobutylethyl, cyclopentylmethyl, cyclopentylethyl, cyclohexylpropyl, 3-cyclohexyl-2-methylpropyl, and the like.

"Halogen" or "halo" means the radical fluoro, bromo, chloro, and/or iodo.

"Haloalkyl" means the lower alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Alkylthio" means the radical —SR, wherein R is a lower alkyl radical as defined herein. Examples of alkylthio radicals include, but are not limited to, methylthio, butylthio, and the like.

"Alkylamino" means the radical —NHR, wherein R is a lower alkyl radical as defined herein. Examples of alkylamino radicals include, but are not limited to, methylamino, (1-ethylethyl)amino, and the like.

"Dialkylamino" means the radical —NR'R", wherein R' and R" are each independently lower alkyl radicals as defined herein. Examples of dialkylamino radicals include, but are not limited to, dimethylamino, methylethylamino, diethylamino, di(1-methylethyl)amino, and the like.

"Alkylaminosulfonyl" means the radical —S(O)$_2$NR'R", wherein R' is lower alkyl as defined herein, and R" is hydrogen or lower alkyl as defined herein. Examples of alkylaminosulfonyl include, but are not limited to methylaminosulfonyl, dimethylaminosulfonyl, and the like.

"Alkylsulfonylamino" means the radical —NS(O)$_2$R', wherein R" is lower alkyl as defined herein. Examples of alkylsulfonylamino include, but are not limited to methylsulfonylamino, ethylsulfonylamino, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl.

"Hydroxyalkylamino means a radical —NRR' wherein R is hydrogen, alkyl or hydroxyalkyl, and R' is hydroxyalkyl as defined herein.

"Heterocyclyl" means a monovalent saturated moiety, consisting of one to three rings, incorporating one, two, or three heteroatoms (chosen from nitrogen, oxygen or sulfur). The heterocyclyl ring may be optionally substituted as defined herein. Examples of heterocyclyl moieties include, but are not limited to, piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"2-Imidazoline", "imidazolin-2-yl" and 4,5-dihydro-1H-imidazol-2-yl", which may be used interchangeably, mean the moiety designated by the structure:

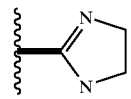

"2-Imidazolinylmethyl", "imidazolin-2-ylmethyl" and 4,5-dihydro-1H-imidazol-2-ylmethyl", which may be used interchangeably, mean the moiety designated by the structure:

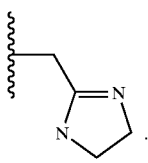

It is to be understood that the double bond in 2-imidazoline and 2-imidazolinylmethyl may assume other resonance forms. The terms 2-imidazoline 2-imidazolinylmethyl include all such resonance forms.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral compound" means a compound with one or more chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When chiral centers are present, the stereoisomers may be characterized by the absolute configuration (R or S) of the chiral centers. Absolute configuration refers to the arrangement in space of the substituents attached to a chiral center. The substituents attached to a chiral center under consideration are ranked in accordance with the Sequence Rule of Cahn, Ingold and Prelog. (Cahn et al. *Angew. Chem. Inter.*, 1966, Edit., 5, 385; errata 511; Cahn et al. *Angew. Chem.*, 1966, 78, 413; Cahn and Ingold, *J. Chem. Soc.* (London), 1951, 612; Cahn et al., *Experientia*, 1956, 12, 81; Cahn, J., *Chem. Educ.*, 1964, 41, 116).

"Tautomers" refers to compounds whose structures differ markedly in arrangement of atoms, but which exist in easy and rapid equilibrium. Compounds of Formula I contain groups that may exist in tautomeric equilibrium. It is to be understood that compounds of Formula I may be depicted as different tautomers.

It should also be understood that when compounds have tautomeric forms, all tautomeric forms are intended to be within the scope of the invention, and the naming of the compounds does not exclude any tautomer form.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Optionally substituted", when used in association with "aryl", phenyl", "benzyl", "benzoyl", "heteroaryl", or "heterocyclyl", means an aryl, phenyl, benzyl, benzoyl, heteroaryl, or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl.

"Leaving group" means the group with the meaning conventionally associated with it in synthetic organic chemistry, i.e., an atom or group displaceable under alkylating conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Inert organic solvent" or "inert solvent" means the solvent inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharaceutical use.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) as defined herein, of the same acid addition salt.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Prodrug" or "pro-drug" means a pharmacologically inactive form of a compound which must be metabolized in vivo, e.g., by biological fluids or enzymes, by a subject after administration into a pharmacologically active form of the compound in order to produce the desired pharmacological effect. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, sulfhydryl, carboxy or carbonyl group respectively. Examples of prodrugs include, but are not limited to, esters (e.g. acetate, dialkylaminoacetates, formates, phosphates, sulfates and benzoate derivatives) and carbamates of hydroxy functional groups (e.g. N,N-dimethyl-carbonyl), esters of carboxyl functional groups (e.g. ethyl esters, morpholinoethanol esters), N-acyl derivatives (e.g. N-acetyl), N-Mannich bases, Schiff bases and enaminones of amino functional groups, oximes, acetals, ketals, and enol esters of ketones and aldehyde functional groups in compounds of Formula I, and the like.

The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action*, by Richard B. Silverman, Academic Press, San Diego, 1992. Chapter 8: "Prodrugs and Drug delivery Systems" pp.352–401; *Design of Prodrugs*, edited by H. Bundgaard, Elsevier Science, Amsterdam, 1985; *Design of Biopharmaceutical Properties through Prodrugs and Analogs*, Ed. by E. B. Roche, American Pharmaceutical Association, Washington, 1977; and *Drug Delivery Systems*, ed. by R. L. Juliano, Oxford Univ. Press, Oxford, 1980.

"Subject" means mammals and non-mammals. Mammals means any member of the Mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

"Pharmacological effect" as used herein encompasses effects produced in the subject that achieve the intended purpose of a therapy. For example, a pharmacological effect would be one that results in the prevention, alleviation or reduction of urinary incontinence in a treated subject.

"Disease state" means any disease, condition, symptom, or indication.

"Treating" or "treatment" of a disease state includes:
(1) preventing the disease state, i.e. causing the clinical symptoms of the disease state not to develop in a subject that may be exposed to or predisposed to the disease state, but does not yet experience or display symptoms of the disease state;
(2) inhibiting the disease state, i.e., arresting the development of the disease state or its clinical symptoms; or
(3) relieving the disease state, i.e., causing temporary or permanent regression of the disease state or its clinical symptoms.

"$\alpha_1$-adrenergic receptors", "$\alpha_{1A}$-adrenergic receptors" (previously known as "$\alpha_{1c}$-adrenergic receptors"), or "$\alpha_{1L}$-adrenergic receptors", used interchangeably with "$\alpha_1$-adrenoceptors", "$\alpha_{1A}$-adrenoceptors" (previously known as "$\alpha_{1C}$-adrenoceptors receptors"), or "$\alpha_{1L}$-adrenoceptors", respectively, refers to a molecule conforming to the seven membrane-spanning G-protein receptors, which under physiologic conditions mediate various actions, for example, in the central and/or peripheral sympathetic nervous system through the binding of the catecholamines, epinephrine and norepinephrine.

"Agonist" means a molecule, such as a compound, a drug, an enzyme activator, or a hormone, that enhances the activity of another molecule or receptor site.

"Urinary Incontinence" is a condition characterized by the involuntary loss of urine, which is objectively demonstrable. It is both a social and hygienic problem. Stated simply, incontinence results from the failure of the bladder and/or the urethra to work properly, or when the coordination of their functions is defective. It is estimated that at least ten million Americans suffer from incontinence. While the prevalence of incontinence is two-fold higher in females, with the greatest incidence in postmenopausal women, it also affects males.

Urinary incontinence can be classified into four basic types: urge, stress, overflow and functional, and as used herein the term "urinary incontinence" encompasses all four types.

Urge incontinence (detrusor instability) is the involuntary loss of urine associated with a strong urge to void. This type of incontinence is the result of either an overactive or hypersensitive detrusor muscle. The patient with detrusor overactivity experiences inappropriate detrusor contractions and increases in intravesical pressure during bladder filling. Detrusor instability resulting from a hypersensitive detrusor (detrusor hyperreflexia) is most often associated with a neurological disorder.

Genuine stress incontinence (outlet incompetence) is the involuntary loss of urine occurring when increases in intra-abdominal pressure cause a rise in intravesical pressure which exceeds the resistance offered by urethral closure mechanisms. Stress incontinent episodes can result from normal activities such as laughing, coughing, sneezing, exercise, or, in severe stress incontinent patients, standing or walking. Physiologically, stress incontinence is often characterized by a descensus of the bladder neck and funneling of the bladder outlet. This type of incontinence is most common in multiparous women, as pregnancy and vaginal delivery can cause loss of the vesicourethral angle and damage to the external sphincter. Hormonal changes associated with menopause may exacerbate this condition.

Overflow incontinence is an involuntary loss of urine resulting from a weak detrusor or from the failure of the detrusor to transmit appropriate signals (sensory) when the bladder is full. Overflow incontinent episodes are characterized by frequent or continuous dribbling of urine and incomplete or unsuccessful voiding.

Functional incontinence, in contrast to the types of incontinence described above, is not defined by an underlying physiological dysfunction in the bladder or urethra. This type of incontinence includes the involuntary loss of urine resulting from such factors as decreased mobility, medications (e.g., diuretics, muscarinic agents, or alpha-1 adrenoceptor antagonists), or psychiatric problems such as depression or cognitive impairment.

"A method of treating or preventing incontinence" refers to the prevention of or relief from the symptoms of incontinence including involuntary voiding of feces or urine, and dribbling or leakage of feces or urine which may be due to one or more causes including, but not limited to, pathology altering sphincter control, loss of cognitive function, over-distention of the bladder, hyper-reflexia and/or involuntary urethral relaxation, weakness of the muscles associated with the bladder, or neurologic abnormalities.

Nomenclature and Structures

In general, the nomenclature used in this Application is based on AUTONOM™ v.4.0, a Beilstein Institute computerized system for the generation of IUPAC systematic nomenclature. The numbering of the indole ring system as used herein is shown by the formula:

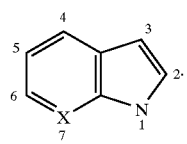

Chemical structures shown herein are prepared using ISIS® v.4.0. Any open valency appearing on a carbon, oxygen or nitrogen atom in the structures herein indicates the presence of a hydrogen.

Compounds

The invention provides compounds of the formula I:

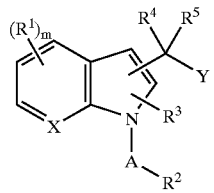

and pharmaceutically acceptable salts and prodrugs thereof, wherein:

m is from 0 to 4;

X is carbon or nitrogen;

Y is a radical of formula i, ii or iii;

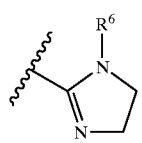

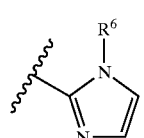

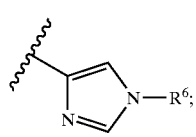

each $R^1$ independently is halogen, haloalkyl, alkyl, hydroxy, alkoxy, cyano, nitro, —S(O)$_n$R$^a$, —NR$^a$R$^b$, —NR$^a$SO$_2$R$^b$, —SO$_2$NR$^a$R$^b$, optionally substituted phenyl, optionally substituted benzyl or optionally substituted benzyloxy, where n is from 0 to 2 and R$^a$ and R$^b$ in each independent occurrence are hydrogen or alkyl;

A is —SO$_2$— or —(C=O)—;

$R^2$ is alkyl or —(CH$_2$)$_p$—NR$^c$R$^d$ where p is from 0 to 3 and R$^c$ and R$^d$ each independently is hydrogen or alkyl; preferably p is 0; and $R^3$, $R^4$, $R^5$ and $R^6$ each independently are hydrogen or alkyl; preferably $R^3$, $R^4$, $R^5$ and $R^6$ are hydrogen.

Where any of $R^1$, $R^2$, $R^3$, $R^4$, $R^5$, $R^6$, R$^a$, R$^b$, R$^c$ and R$^d$ are alkyl, they are preferably lower alkyl, i.e. $C_1$–$C_6$alkyl, and more preferably $C_1$–$C_4$alkyl.

In certain embodiments of the invention, X is carbon and Y is a 2-imidazolinylmethyl moiety of formula i located at the 3-position of the indole ring system, and $R^3$ is located at the 2-position of the indole ring system. In such embodiments compounds of formula I may be represented by formula II:

II:

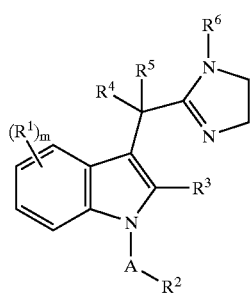

wherein m, A, $R^1$, $R^2$, $R^3$, $R^4$, $R^5$ and $R^6$ are as defined herein. In one preferred embodiment, A is —$SO_2$—, $R^2$ is lower alkyl, and $R^4$, $R^5$ and $R^6$ are hydrogen, such that the subject compounds may be more specifically represented by the formula III:

III:

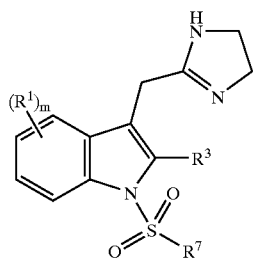

wherein $R^7$ is lower alkyl, and m, $R^1$, $R^2$ and $R^3$ are as defined herein. In another preferred embodiment, A is —(C=O)—, $R^2$ is $(CH_2)_p$—$NR^cR^d$ with p=0, and $R^4$, $R^5$ and $R^6$ are hydrogen, such that compounds of the invention may be represented by the formula IV:

IV:

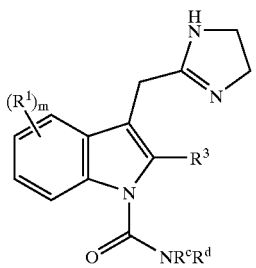

wherein m, $R^1$, $R^3$, $R^c$ and $R^d$ are as defined herein.

Representative compounds in accordance with the invention are shown in Table 1 together with mass spectrum M+H and the experimental examples (described below) associated with each compound.

TABLE 1

| | Name (Autonom ®) | Structure | Example | M + H |
|---|---|---|---|---|
| 1 | 4-Chloro-3-(4,5-dihydro-1H-imidazol-2-ylmethyl)-1-methanesulfonyl-1H-indole | 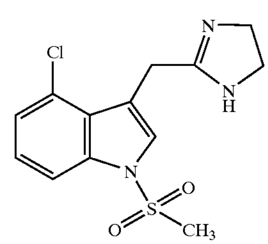 | 1 | 312 |
| 2 | 7-Chloro-3-(4,5-dihydro-1H-imidazol-2-ylmethyl)-1-methanesulfonyl-1H-indole | 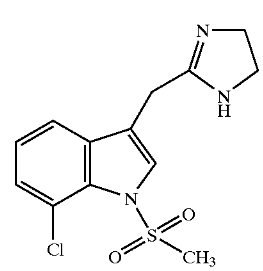 | 1 | 312 |

TABLE 1-continued

| Name (Autonom ®) | Structure | Example | M + H |
|---|---|---|---|
| 3 5-Chloro-3-(4,5-dihydro-1H-imidazol-2-ylmethyl)-1-methanesulfonyl-1H-indole | | 1 | 312 |
| 4 6-Chloro-3-(4,5-dihydro-1H-imidazol-2-ylmethyl)-1-methanesulfonyl-1H-indole | | 1 | 312 |
| 5 4-Bromo-3-(4,5-dihydro-1H-imidazol-2-ylmethyl)-1-methanesulfonyl-1H-indole | | 1 | 356 |
| 6 6-Bromo-3-(4,5-dihydro-1H-imidazol-2-ylmethyl)-1-methanesulfonyl-1H-indole | | 1 | 356 |
| 7 4-Chloro-3-(4,5-dihydro-1H-imidazol-2-ylmethyl)-1-ethanesulfonyl-1H-indole | | 1 | 325 |

TABLE 1-continued

| Name (Autonom ®) | Structure | Example | M + H |
|---|---|---|---|
| 8 4-Chloro-3-(4,5-dihydro-1H-imidazol-2-ylmethyl)-1-methanesulfonyl-6-methoxy-1H-indole | | 3 | 342 |
| 9 4-Chloro-3-(4,5-dihydro-1H-imidazol-2-ylmethyl)-6-fluoro-1-methanesulfonyl-1H-indole | | 3 | 330 |
| 10 4-Chloro-3-(4,5-dihydro-1H-imidazol-2-ylmethyl)-1-(propane-2-sulfonyl)-1H-indole | | 1 | 340 |
| 11 3-(4,5-Dihydro-1H-imidazol-2-ylmethyl)-4-fluoro-1-methanesulfonyl-1H-indole | | 1 | 296 |
| 12 3-(4,5-Dihydro-1H-imidazol-2-ylmethyl)-6-fluoro-1-methanesulfonyl-1H-indole | | 1 | 295 |

TABLE 1-continued

| Name (Autonom ®) | Structure | Example | M + H |
|---|---|---|---|
| 13  3-(4,5-Dihydro-1H-imidazol-2-ylmethyl)-5-fluoro-1-methanesulfonyl-1H-indole | | 1 | 296 |
| 14  4-Chloro-3-(4,5-dihydro-1H-imidazol-2-ylmethyl)-5-fluoro-1-methanesulfonyl-1H-indole | | 3 | 330 |
| 15  3-(4,5-Dihydro-1H-imidazol-2-ylmethyl)-1-methanesulfonyl-4-methyl-1H-indole | | 1 | 292 |
| 16  3-(4,5-Dihydro-1H-imidazol-2-ylmethyl)-1-methanesulfonyl-1H-indole | | 4 | |
| 17  3-(4,5-Dihydro-1H-imidazol-2-ylmethyl)-1-methanesulfonyl-5-methoxy-2-methyl-1H-indole | | 4 | 321 |
| 18  3-(4,5-Dihydro-1H-imidazol-2-ylmethyl)-1-methanesulfonyl-4-methoxy-1H-indole | | 1 | 308 |

TABLE 1-continued

| Name (Autonom ®) | Example | M + H |
|---|---|---|
| 19 3-(4,5-Dihydro-1H-imidazol-2-ylmethyl)-1-methanesulfonyl-6-methoxy-1H-indole | 1 | 308 |
| 20 3-(4,5-Dihydro-1H-imidazol-2-ylmethyl)-1-methanesulfonyl-5-methoxy-4-methyl-1H-indole | 1 | 322 |
| 21 4-Chloro-3-(4,5-dihydro-1H-imidazol-2-ylmethyl)-1-methanesulfonyl-2-methyl-1H-indole | 2 | 326 |
| 22 6-Bromo-3-(4,5-dihydro-1H-imidazol-2-ylmethyl)-5-fluoro-1-methanesulfonyl-1H-indole | 1 | 374 |
| 23 4-Chloro-3-(1H-imidazol-2-ylmethyl)-1-methanesulfonyl-1H-indole | 1 | 310 |

TABLE 1-continued

| Name (Autonom ®) | Structure | Example | M + H |
|---|---|---|---|
| 24 4-Chloro-3-(1H-imidazol-4-ylmethyl)-1-methanesulfonyl-1H-indole | | 9 | 310 |
| 25 4-Chloro-3-(4,5-dihydro-1H-imidazol-2-ylmethyl)-indole-1-carboxylic acid amide | | 7 | 277 |
| 26 4-Chloro-3-(4,5-dihydro-1H-imidazol-2-ylmethyl)-indole-1-carboxylic acid methylamide | | 6 | M + H 291 |
| 27 4-Chloro-3-(4,5-dihydro-1H-imidazol-2-ylmethyl)-indole-1-carboxylic acid dimethylamide | | 5 | 305 |
| 28 3-(4,5-Dihydro-1H-imidazol-2-ylmethyl)-1-methanesulfonyl-1H-pyrrolo[2,3-b]pyridine | | 8 | 279 |

General Synthetic Reaction Schemes

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. Where necessary, conventional protecting group techniques were used as described by Greene et al., *Protecting Groups in Organic Synthesis*, 3rd Ed., Wiley Interscience, 1999. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

Schemes A through F describe general methods for preparation of compounds of formula I. Schemes A and B illustrate synthetic routes to indole compounds usable in preparation of compounds of formula I. Schemes C and D show methods of preparing compounds of formula I that fall within the embodiments of formula III above. Scheme E relates a procedure for preparation of compounds of formula I that fall within the embodiments of formula IV above. Scheme F illustrates a procedure that may be used in the preparation of 7-azaindole compounds of formula I wherein X is nitrogen. Specific examples in accordance with Schemes A–F are provided below in the Experimental portion of this disclosure.

Referring first to Scheme A, there is shown a synthetic route for preparation of substituted indoles (i.e., where X in formula I is carbon) usable in preparation of the subject compounds. In Scheme A, R is any lower alkyl and may be the same or different in each occurrence, and m, $R^1$ and $R^3$ are as defined herein.

SCHEME A

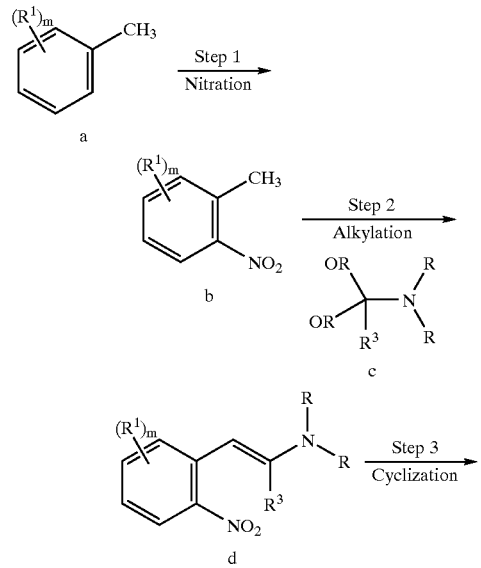

-continued

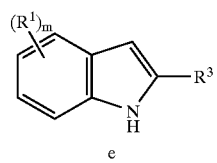

In step 1 of Scheme A, a toluene compound a is nitrated by treatment of compound a with nitric acid in the presence of sulfuric acid at reduced temperature to produce an ortho nitrotoluene b. Alkylation of a benzylic carbon of compound b occurs in step 2 by an condensation reaction with acetal c to yield condensation product d. The acetal compound c may be in the form of an N,N-dialkyl amide dialkyl acetal c, such as N,N-dimethyl formamide diisopropyl acetal or N,N-dimethyl acetamide diisopropyl acetal, and the condensation may be carried out by heating under dry, polar aprotic conditions. In step 3 a cyclization is carried out to form indole compound e from condensation product d. This cyclization may be achieved under reducing conditions by use of Raney Nickel and hydrazine hydrate under mild, polar protic conditions. Indole compound e may subsequently be used to prepare compounds of formulas I and IV as shown in Schemes C and E and described below.

Scheme B represents another synthetic route for preparation of substituted indoles suitable for use in the subject compounds, wherein R is any lower alkyl and may be the same or different in each occurrence, PG is a protecting group, and m, $R^1$ and $R^3$ are as defined herein.

SCHEME B

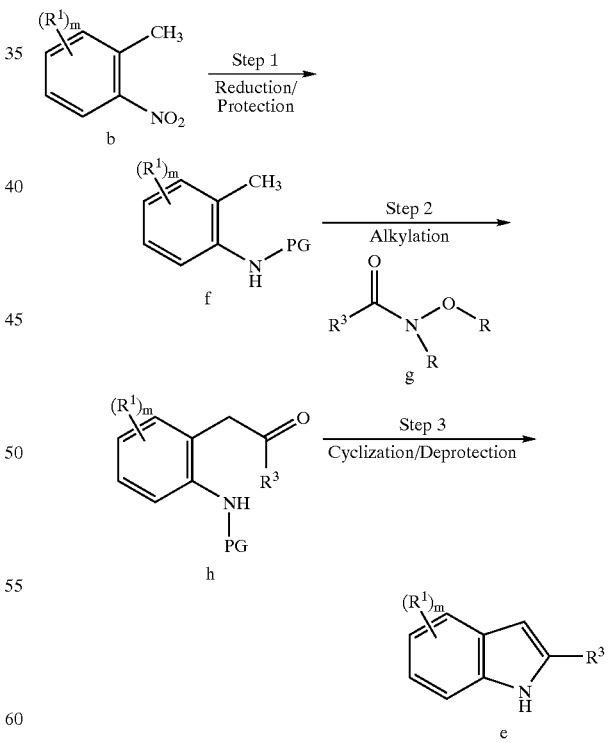

In step 1 of Scheme B, an ortho nitrotoluene b is subject to reduction via treatment with $SnCl_2$, $H_2$/Pd or other reducing reagent to afford an aniline compound (not shown), which is then protected by BOC or other suitable amine protection chemistry to provide protected aniline f. Compound b may be prepared as described in Scheme A or obtained commercially. The protected aniline f is alkylated by treatment with alkyl lithium or other strong base, and then reaction with an N-alkyl-N-alkoxy amide g to yield a keto-substituted compound h. The keto-compound h may then be treated with acid to effect deprotection and cyclization to provide indole compound e.

Scheme C illustrates one synthetic route to compounds of formula III wherein R is any lower alkyl and may be the same or different in each occurrence, X is halo and may be the same or different in each occurrence, and m, $R^3$, $R^4$, $R^5$ and $R^7$ are as described herein.

SCHEME C

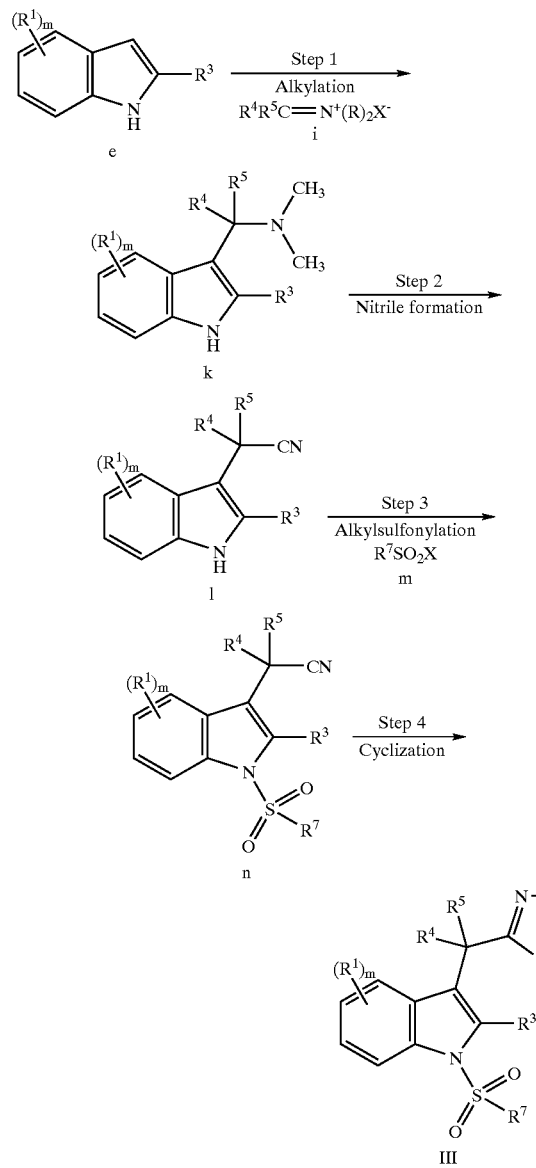

In step 1 of Scheme C, indole e (prepared as described in Scheme A or B) is alkylated at the 3-position by reaction with an imminium salt j under polar aprotic conditions to yield an aminoalkyl indole k. The iminium compound j may comprise, for example, N,N-dimethyleneiminium halide where $R^4$ and $R^5$ are hydrogen.

In step 2, the aminoalkyl indole compound k is converted to a nitrile compound l via heating with alkalai metal cyanide such as NaCN in a polar aprotic solvent system.

The nitrile compound l may then be treated with alkalai metal hydride or like base, followed by an alkylsulfonyl halide reagent m to provide an alkylsulfonylated nitrile compound n. Where $R^7$ is methyl, reagent m may comprise, for example, methanesulfonyl chloride. The alkylsulfonylation of step 3 may be performed under dry polar aprotic solvent conditions.

In step 4, the alkylsulfonylated nitrile compound n of step 3 is exposed to acid and EtOH to form an imidate, and then treated with ethylene diamine to effect cyclization to form an imidazolinyl group and provide a compound of formula III, which represents specific embodiments of compounds of formula I as described above.

Several variations on the procedure of Scheme C may be used to provide various embodiments compounds of the invention. In one such variation, the alkylsulfonylated nitrile compound n of step 3 may, after acid treatment, be reacted with aminoacetaldehyde dimethyl acetal instead of ethylene diamine, to afford an imidazol group (i.e., a group of formula ii) instead of the imidazolinyl group shown in Scheme C. In other variations of Scheme C, the indole nitrogen of compound e or k may be protected to allow aromatic substitution(s) at positions 4–7 of the indole ring, and then subsequently deprotected to allow alkylsulfonylation in step 3. The alkylsulfonylation of step 3 may be carried out prior to nitrile formation when the indole nitrogen is suitably protected. Other variations on the procedures of Scheme C and the other reaction schemes herein will suggest themselves to those skilled in the art.

Referring to Scheme D there is shown a synthetic procedure wherein R is any lower alkyl and may be the same or different in each occurrence, and m, $R^1$, $R^3$ and $R^7$ are as defined herein. Scheme D represents a preferred synthetic procedure for embodiments in which $R^3$ is alkyl and $R^4$ and $R^5$ are hydrogen.

SCHEME D

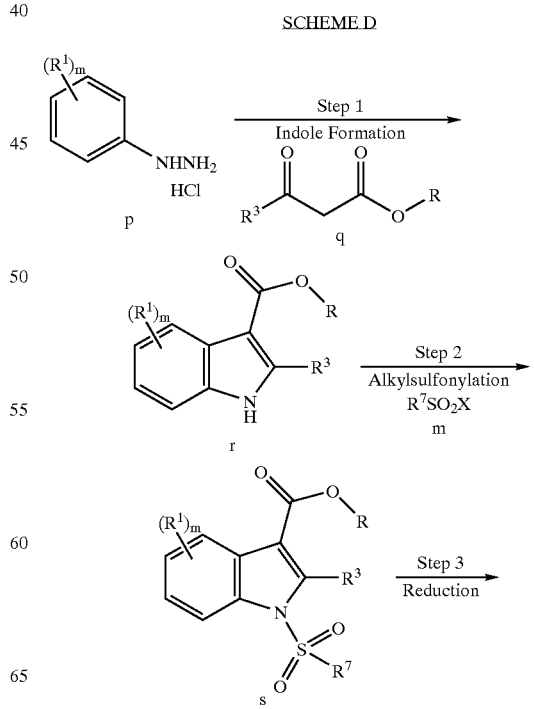

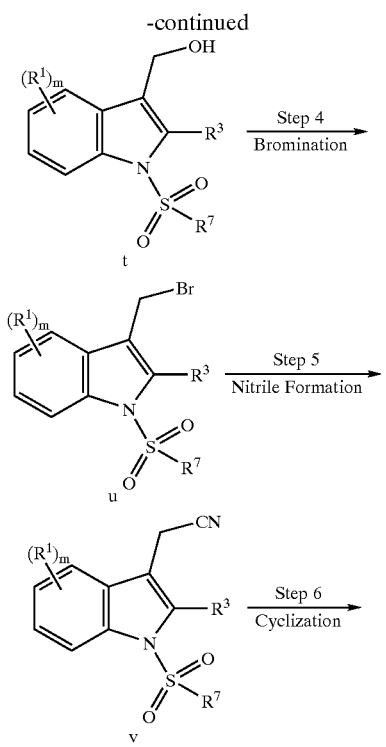

In step 1 of Scheme D, a phenyl hydrazine p is reacted with a beta keto ester q under acidic conditions to provide a carboxyester indole r.

The carboxyester indole compound r may then in step 2 be treated with base and reacted with an alkylsulfonyl halide m, in the manner described above in Scheme C, to yield an alkylsulfonylated compound s.

In step 3, carboxyester compound s is subject to reduction to afford a hydroxymethyl indole t. This reduction may be performed using a dialkylaluminum hydride reducing agent such as "DIBAL" under dry, polar aprotic solvent conditions with reduced temperature and inert atmosphere.

In step 4 a bromination or other halogenation is carried out to convert the hydroxymethyl indole t of step 3 to a bromomethyl indole compound u. Bromination in this case may be performed using phosphorus tribromide and dry, polar aprotic solvent conditions at reduced temperature.

The bromomethyl indole compound u is then used to prepare a cyanomethyl indole compound v in step 5 by reaction with alkalai metal nitrile salt in the manner described above for Scheme C. Step 6 of Scheme D involves a cyclization by reaction of the cyanomethyl indole v of step 5 with ethylene diamine as described in Scheme C, to provide a compound of formula III.

As in the case of Scheme C, many variations on the procedure of Scheme D are possible and may be used to provide compounds in accordance with the invention. For example, alkylsulfonylation may be carried out prior to nitrile formation in cases where the indole nitrogen is suitably protected. Aminoacetaldehyde dimethyl acetal may be used in place of ethylene diamine in step 6 to provide an imidazol group instead of an imidazolinyl group as noted above.

Referring now to Scheme E, there are shown reaction procedures for preparation of compounds of the invention that correspond to formula IV, wherein m, $R^3$, $R^4$, $R^5$, $R^c$ and $R^d$ are as described herein. Step 1 of Scheme E diverges along three paths shown as steps 1a, 1b and 1c which respectively correspond to embodiments where $R^c$ and $R^d$ are both hydrogen, where $R^c$ is hydrogen and $R^d$ is alkyl, and where both where $R^c$ and $R^d$ are alkyl.

SCHEME E

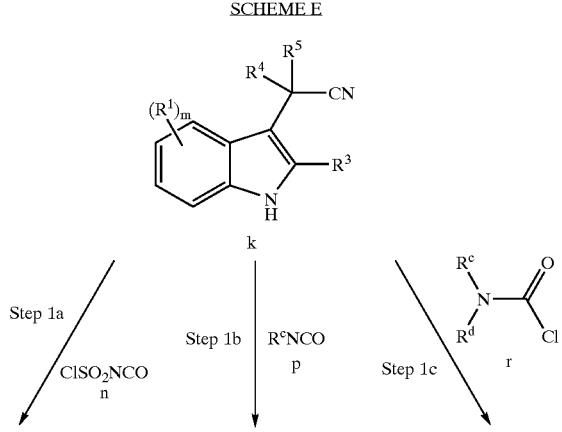

-continued

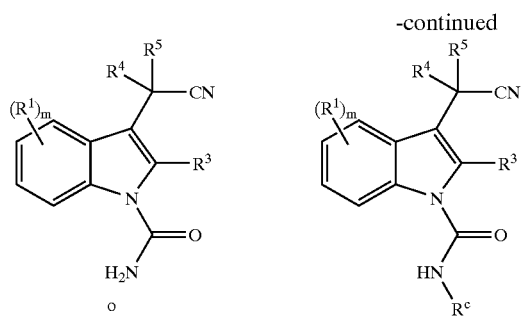

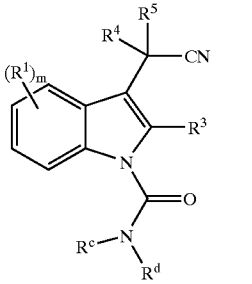

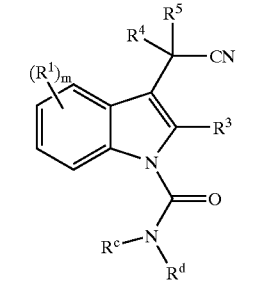

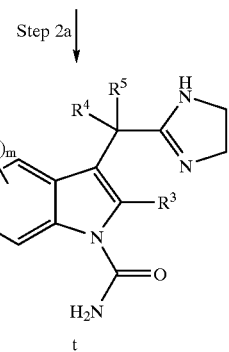

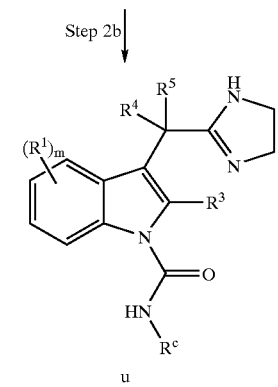

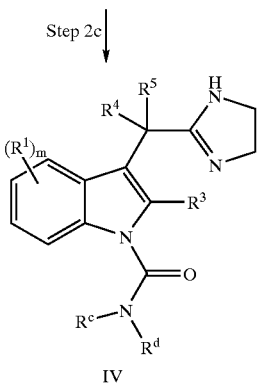

In step 1a of Scheme E, a cyanoalkyl indole compound k, which may be prepared as described above in Scheme C, is reacted with a chlorosulfonyl isocyanate n under dry, polar aprotic solvent conditions to form carboxylic acid amide compound o. Alternatively, cyanoalkyl indole compound k may be treated with an alkyl lithium reagent (not shown) followed by an alkyl isocyanate p under dry, polar aprotic solvent conditions in step 1b to yield a carboxylic acid alkylamide compound q. Step 1c provides yet another alternative in which cyanoalkyl indole compound k is reacted with an alkyl lithium reagent followed by a N,N-dialkyl carbamyl chloride r under dry, polar aprotic solvent conditions to provide a carboxylic acid dialkylamide compound s.

In steps 2a–2c, the carboxylic amide compounds o, q, and s may be treated with HCl/EtOH followed by ethylene diamine, in the manner described in step 4 of Scheme C above, to achieve a cyclization to form an imidazolinyl group and respectively provide compounds of formulas t, u and IV. Compounds of formula IV represent a specific embodiment of compounds of formula I, and compounds t and u in turn represent specific embodiments of formula IV.

Scheme F below illustrates a synthetic procedure usable for preparation of azaindole compounds in accordance with the invention, where X is halo or other leaving group and $R^1$ and $R^7$ in Scheme F being as defined above.

SCHEME F

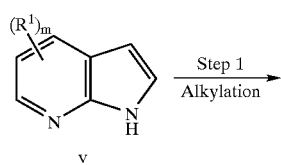

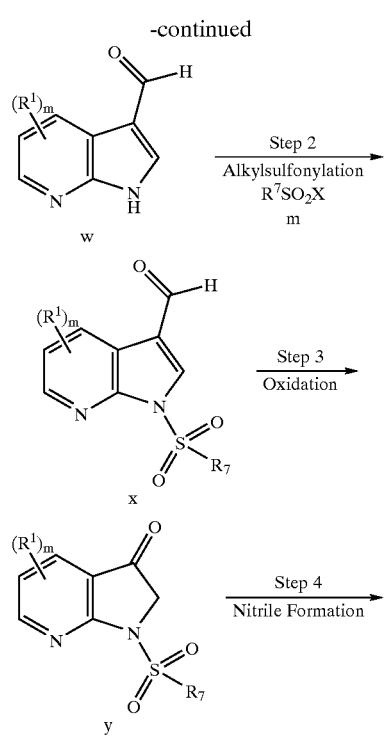

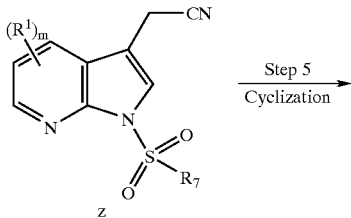

-continued

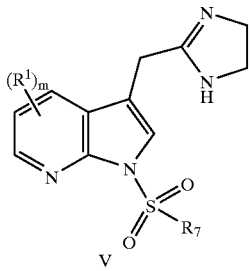

V

In step 1 of Scheme F, a 7-azaindole compound v is alkylated by heating with hexamethylenetetramine under acidic conditions to provide an azaindole aldehyde compound w.

The aldehyde compound w is then treated with an alkalai metal hydride or like base under polar protic solvent conditions, followed by reaction with an alkylsulfonyl halide m to provide an alkylsulfonylated azaindole x.

In step 3, alkylsulfonyl halide m is treated with a mild oxidizing agent such as a perbenzoic acid, in polar aprotic solvent, to afford a pyrrolopyridinone compound y.

A nitrile formation reaction may then be carried out in step 4 by reaction of pyrrolopyridinone compound y with a dialkoxycyanomethyl phosphonate (not shown) to afford a cyanomethyl azaindole compound z.

The cyanomethyl azaindole compound z may be treated with HCl/EtOH followed by ethylene diamine, in the manner described in step 4 of Scheme C above, to form an imidazolinyl group and yield a compound of formula V, which represents a specific embodiment of compounds of formula I.

As noted above many variations on the procedure of Scheme F may be used as required to prepare different embodiments of the subject compounds. In step 2, for example, alkylsulfonylation may instead be replaced by reaction with a chlorosulfonyl isocyanate, alkyl isocyanate or N,N-dialkyl carbamyl compound as shown in Scheme E above to provide corresponding carboxylic acid amide compounds.

General Utility

The compounds of the present invention have selective alpha-1A/L adrenergic selective activity and as such are expected to be useful in the treatment of various disease states, such as urinary incontinence; nasal congestion; sexual dysfunction, such as ejaculation disorders and priapism; CNS disorders such as depression, anxiety, dementia, senility, Alzheimer's, deficiencies in attentiveness and cognition, and eating disorders such as obesity, bulimia, and anorexia.

Urinary incontinence (UI) is a condition defined as the involuntary loss of urine to such an extent as to become a hygienic or social concern to the patient. Involuntary loss of urine occurs when pressure inside the bladder exceeds retentive pressure of the urethral sphincters (intraurethral pressure). Four major types of urinary incontinence have been defined based on symptoms, signs and condition: stress, urge, overflow and functional incontinence.

Stress urinary incontinence (SUI) is the involuntary loss of urine during coughing, sneezing, laughing, or other physical activities. The present methods to treat SUI include physiotherapy and surgery. Treatment with pharmaceutical agents is limited to the use of non selective-adrenergic agonists like phenylproanolamine and midodrine. The rationale for the use of adrenergic agonists for the treatment of SUI is based on physiological data indicating an abundant noradrenergic input to smooth muscle of the urethra.

Urge incontinence (detrusor instability) is the involuntary loss of urine associated with a strong urge to void. This type of incontinence is the result of either an overactive or hypersensitive detrusor muscle. The patient with detrusor overactivity experiences inappropriate detrusor contractions and increases in intravesical pressure during bladder filling. Detrusor instability resulting from a hypersensitive detrusor (detrusor hyperreflexia) is most often associated with a neurological disorder.

Overflow incontinence is an involuntary loss of urine resulting from a weak detrusor or from the failure of the detrusor to transmit appropriate signals (sensory) when the bladder is full. Overflow incontinent episodes are characterized by frequent or continuous dribbling of urine and incomplete or unsuccessful voiding.

Functional incontinence, in contrast to the types of incontinence described above, is not defined by an underlying physiological dysfunction in the bladder or urethra. This type of incontinence includes the involuntary loss of urine resulting from such factors as decreased mobility, medications (e.g., diuretics, muscarinic agents, or alpha-1 adrenoceptor antagonists), or psychiatric problems such as depression or cognitive impairment.

The compounds of this invention are also particularly useful for the treatment of nasal congestion associated with allergies, colds, and other nasal disorders, as well as the sequelae of congestion of the mucous membranes (for example, sinusitis and otitis media), with less or no undesired side effects.

These and other therapeutic uses are described, for example, in *Goodman & Gilman's, The Pharmacological Basis of Therapeutics*, ninth edition, McGraw-Hill, New York, 1996, Chapter 26:601–616; and Coleman, R. A., *Pharmacological Reviews*, 1994, 46:205–229.1

Testing

General Strategy for Identifying Alpha-1A/L-adrenocettor Agonists:

In Vitro:

The inhibitory activity of compounds of this invention in vitro was examined using fluorescent dye determination of intracellular calcium concentrations as described in the Examples below. Alpha-1A/L-adrenoceptor agonist activity was determined in vitro and in vivo.

In Vitro:

The activity of potential alpha-1A/L activity in vitro was determined by evaluating the potency and relative intrinsic activity (relative to norepinephrine or phenylephrine) of standard and novel compounds to contract isolated rabbit bladder neck strips (alpha-1A/L-adrenoceptor) and isolated rat aortic rings (alpha-1D adrenoceptor).

In Vivo:

Standard and novel compounds which selectively contracted rabbit bladder neck strips were subsequently evaluated in vivo in anesthetized female micropigs to assess urethral activity relative to diastolic blood pressure effects. Compounds with the desired activity in anesthetized pigs were evaluated in conscious female micropigs instrumented with telemetry to measure diastolic blood pressure and a strain-gage transducer to measure urethral tension.

Administration and Pharmaceuticl Compostion

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Example 5.

The following preparations and examples are given to enable those skilled in the art to more clearly understand and to practice the present invention. They should not be considered as limiting the scope of the invention, but merely as being illustrative and representative thereof.

Efforts have been made to ensure accuracy with respect to numbers used (e.g., amounts, temperatures, etc.), but some experimental error and deviation should, of course, be allowed for as well as due to differences such as, for example, in calibration, rounding of numbers, and the like.

EXAMPLES

The following preparations and examples are given to enable those skilled in the art to more clearly understand and to practice the present invention. They should not be considered as limiting the scope of the invention, but merely as being illustrative and representative thereof.

Example 1

6-Bromo-3-(4,5-dihydro-1H-imidazol-2-ylmethyl)-5-fluoro-1-methanesulfonyl-1H-indole The synthetic procedures described in this Example were carried out according to the process shown in Scheme G.

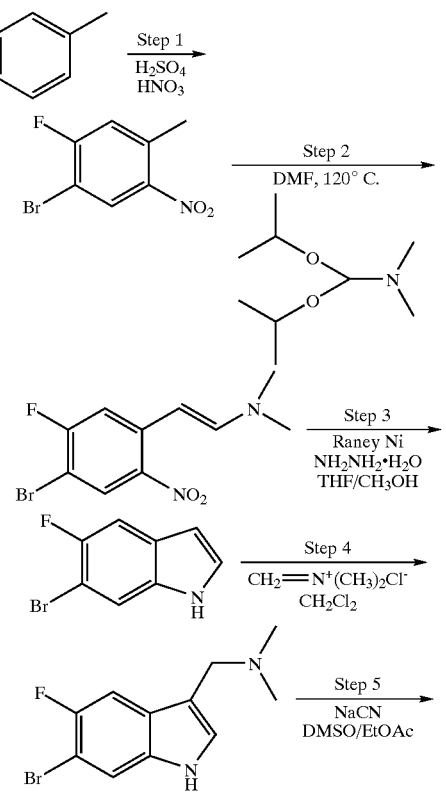

39

-continued

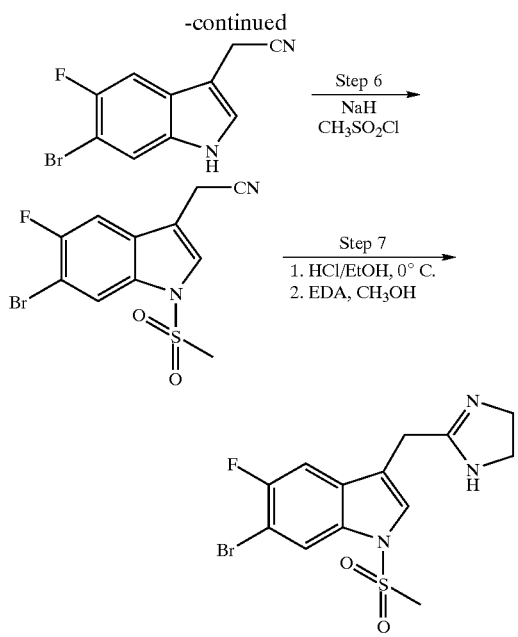

Step 1
1-Bromo-2-Fluoro-4-methyl-5-nitrobenzene

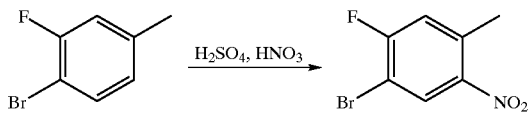

To a solution of 1-Bromo-2-fluoro-4-methyl-benzene (5.35 g, 28.30 mmol) in concentrated sulfuric acid (25 ml) was added concentrated nitric acid(9 ml) dropwise while maintaining an internal reaction temperature below 20° C. The reaction mixture was stirred at 0° C. for 10 minutes and poured into ice water. The resulting mixture was extracted three times with ether. The combined ether extracts were washed with brine, dried (anhydrous sodium sulfate) and concentrated under reduced pressure. The residue was purified by flash column chromatography over silica gel eluting with 2 to 3% ethyl acetate in hexanes give 1-Bromo-2-fluoro-4-methyl-5-nitro-benzene as a white solid (5.21g, 78%).

$^1$H NMR (CDCl$_3$) d:2.60 (s, 3H), 7.11 (d, 1H, J=8.6 Hz), 8.28 (d, 1H, J=6.4 Hz).

Step 2
[2-(4-Bromo-5-fluoro-2-nitrophenyl)-vinyl]-dimethylamine

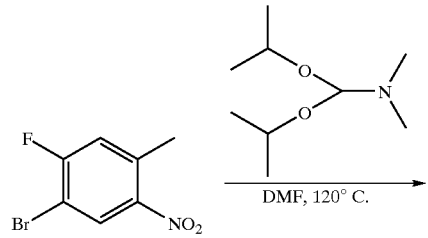

40

-continued

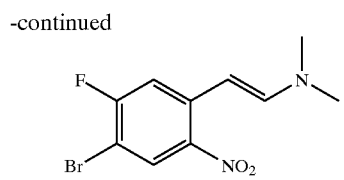

A mixture of N,N-dimethyl formamide diisopropyl acetal (1.7 ml, 8.13 mmol) and 1-Bromo-2-fluoro-4-methyl-5-nitro-benzene (1.538 g, 6.57 mmoles) in dry dimethylformamide (10 ml) was heated at 120–125° C. for 1.5 hours. The resulting dark red solution was concentrated under reduced pressure and partitioned between ethyl acetate and water. The organic extract was washed with brine, dried (anhydrous sodium sulfate), and concentrated under reduced pressure to give [2-(4-Bromo-5-fluoro-2-nitro-phenyl)-vinyl]-dimethyl-amine as a dark red solid.

$^1$H NMR (CDCl$_3$) d:2.95 (s, 6H), 5.92 (dd, 1H, J=13.3 Hz, 1.8 Hz), 6.98 (d, 1H, J=13.3 Hz) 7.13 (d, 1H, J=10.8 Hz), 8.15 (d, 1H, J=6.86 Hz), M+H: 271.

Step 3
6-Bromo-5-fluoroindole

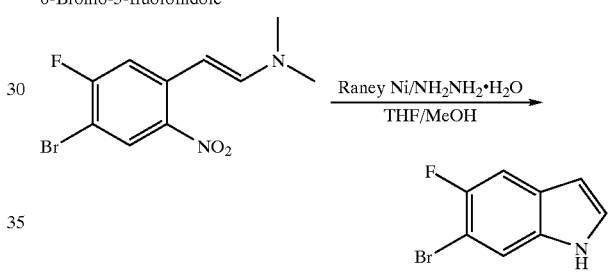

Synthesis of 6-Bromo-5-fluoroindole was carried out in this step according to the procedure reported by A. D. Batcho and W. Leimgruber; *Org. Synth.* 1985, 63, 214. A mixture of hydrazine hydrate (1.30 ml, 26.8 mmoles), crude [2-(4-Bromo-5-fluoro-2-nitro-phenyl)-vinyl]-dimethyl-amine as from step 2 and Raney nickle in tetrahydrofuran (30 ml) and methanol (30 ml) was stirred at room temperature over night. The catalyst was removed by filtration through celite and the filtrate was concentrated under reduced pressure. The residue was partitioned between ethyl acetate and 0.1N hydrogen chloride solution. The organic extract was washed with brine, dried (anhydrous sodium sulfate), and concentrated under reduced pressure. The residue was purified by flash column chromatography over silica gel eluting with 10% ethyl acetate in hexane to give 6-Bromo-5-fluoro-1H-indole as a light green solid (0.865 g, 61%). $^1$H NMR (CDCl$_3$) d: 6.49–6.51 (m, 1H), 7.23–7.26 (m, 1H), 7.36 (d, 1H, J=9.2 Hz), 7.56 (dd, 1H, J=5.6 Hz, 0.9 Hz), 8.14 (bs, 1H).

Step 4
(6-Bromo-5-fluoro-1H-indol-3-ylmethyl)-dimethylamine

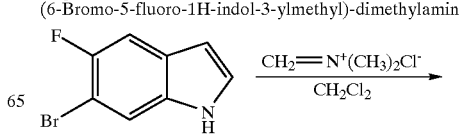

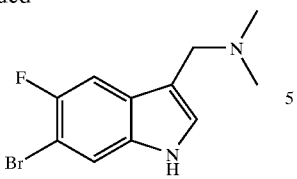

To a solution of 6-bromo-5-fluoro-1H-indole (0.86 g, 4.02 mmol) in CH$_2$Cl$_2$ (30 ml) was added N,N-dimethyl methyleneiminium chloride (0.5 g, 5.34 mmol). The mixture was stirred at room temperature overnight and a aqueous sodium hydroxide (0.22 g, 5.50 mmol, 100 ml water) was added. The aqueous solution was extracted into ethyl acetate. The organic extract was dried (anhydrous sodium sulfate) and concentrated under reduced pressure to give (6-Bromo-5-fluoro-1H-indol-3-ylmethyl)-dimethyl-amine as a light green solid (1.06 g).

$^1$H NMR (DMSO) d: 2.12 (s, 6H), 3.48 (s, 2H), 7.34 (s, 1H), 7.50(d, 1H, J=9.9 Hz), 7.62 (d, 1H, J=6.0 Hz). M−H: 269.

Step 5
(6-Bromo-5-fluoro-1H-indol-3-yl)-acetonitrile

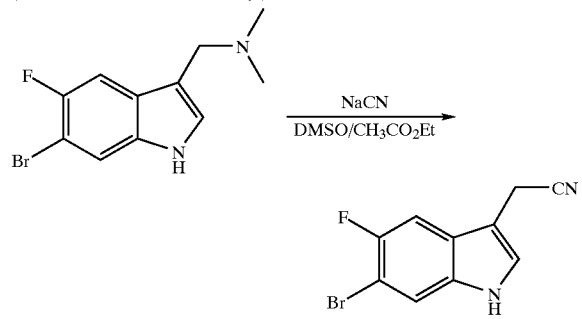

A mixture of (6-Bromo-5-fluoro-1H-indol-3-ylmethyl)-dimethyl-amine (1.0 g) and sodium cyanide (0.54 g, 11.02 mmol) in ethyl acetate (1.8 ml) and methylsulfoxide (16 ml) was heated at 80° C. for 24 hrs then partitioned between ethyl acetate and water. The organic extract was washed with brine, dried (anhydrous sodium sulfate), concentrated under reduced pressure. The residue was purified by flash column chromatography over silica gel eluting with 20% ethyl acetate in hexane to give (6-Bromo-5-fluoro-1H-indol-3-yl)-acetonitrile as a yellow solid (0.41 g, 44%). $^1$H NMR (CDCl$_3$) d: 3.78 (d, 2H, J=1.0 Hz), 7.27 (dd, 1H, J=1.2 Hz), 7.31 (d, 1H, J=8.8 Hz, 7.58 (d, 1H, J=5.5 Hz), 8.23 (bs, 1H).

Step 6
(6-Bromo-5-fluoro-1-methanesulfonyl-1H-indol-3-yl)-acetonitrile

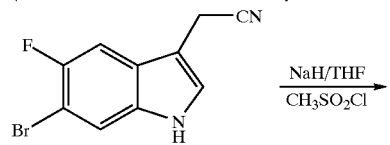

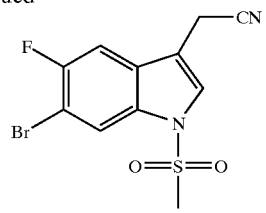

To a solution of (6-Bromo-5-fluoro-1H-indol-3-yl)-acetonitrile (0.205 g, 0.81 mmol) in anhydrous tetrahydrofuran (10 ml), was added sodium hydride (0.1 g, 2.5 mmol, 60% in mineral oil) at 0° C. After stirring for 10 minutes, methanesulfonyl chloride (0.13 ml, 1.68 mmol) was added dropwise. The reaction mixture was stirred at room temperature for 24 h then partitioned between ethyl acetate and water. The organic extract was washed with brine, dried (anhydrous sodium sulfate), and concentrated under reduced pressure. The residue was purified by flash column chromatography over silica gel eluting with 30% ethyl acetate in hexane to give (6-Bromo-5-fluoro-1-methanesulfdnyl-1H-indol-3-yl)-acetonitrile as a yellow solid, (0.22 g, 82%). $^1$H NMR (CDCl$_3$) d: 3.59 (s, 3H), 4.15 (d, 2H, J=1.1 Hz), 7.75(s, 1H), 7.79 (d, 1H, J=9.0 Hz) 8.11 (d, 1H, J=5.8 Hz).

Step 7
6-Bromo-3-(4,5-dihydro-1H-imidazol-2-ylmethyl)-5-fluoro-1-methanesulfonyl-1H-indole

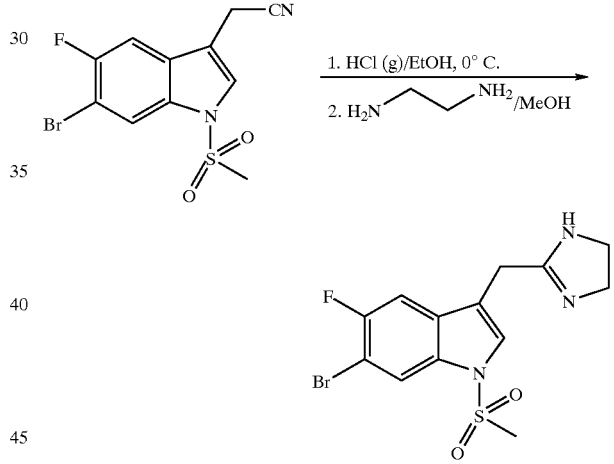

Hydrogen chloride gas was bubbled through a cold (0° C.) suspension of (6-Bromo-5-fluoro-1-methanesulfonyl-1H-indol-3-yl)-acetonitrile (0.215 g, 0.65 mmol) in anhydrous ethanol (20 ml) for 15 minutes. The reaction mixture was refrigerated for 72 hours and the solvent was removed under reduced pressure. The solid residue was re-dissolved in anhydrous methanol (10 ml), and ethylene diamine (0.05 ml, 0.77 mmol) was added. The reaction mixture was heated to reflux for 24 hours and the solvent was removed under reduced pressure. The resulting residue was purified by flash column chromatography over silica gel eluting with 7% methanol in dichloromethane with 0.1% concentrated ammonium hydroxide to give 6-Bromo-3-(4,5-dihydro-1H-imidazol-2-ylmethyl)-5-fluoro-1-methanesulfonyl-1H-indole, which was recrystallized from methanol and ether (0.133 g, 55%). $^1$H NMR (DMSO) d: 3.56 (s, 3H), 3.82(s, 4H), 4.07 (s, 2H), 7.84 (s, 1H), 7.90 (d, 1H, J=9.1 Hz), 8.10 (d, 1H, J=5.8 Hz), 10.23 (bs, 1H). M+H: 374.

The following compounds were also synthesized by the procedure of Example 1:

4-Chloro-3-(4,5-dihydro-1H-imidazol-2-ylmethyl)-1-methanesulfonyl-1H-indole;

5-Chloro-3-(4,5-dihydro-1H-imidazol-2-ylmethyl)-1-methanesulfonyl-1H-indole;

6-Chloro-3-(4,5-dihydro-1H-imidazol-2-ylmethyl)-1-methanesulfonyl-1H-indole;

7-Chloro-3-(4,5-dihydro-1H-imidazol-2-ylmethyl)-1-methanesulfonyl-1H-indole;

4-Bromo-3-(4,5-dihydro-1H-imidazol-2-ylmethyl)-1-methanesulfonyl-1H-indole;

6-Bromo-3-(4,5-dihydro-1H-imidazol-2-ylmethyl)-1-methanesulfonyl-1H-indole;

-(4,5-Dihydro-1H-imidazol-2-ylmethyl)-4-fluoro-1-methanesulfonyl-1H-indole;

3-(4,5-Dihydro-1H-imidazol-2-ylmethyl)-5-fluoro-1-methanesulfonyl-1H-indole;

3-(4,5-Dihydro-1H-imidazol-2-ylmethyl)-6-fluoro-1-methanesulfonyl-1H-indole;

3-(4,5-Dihydro-1H-imidazol-2-ylmethyl)-1-methanesulfonyl-4-methyl-1H-indole;

3-(4,5-Dihydro-1H-imidazol-2-ylmethyl)-1-methanesulfonyl-6-methoxy-1H-indole;

3-(4,5-Dihydro-1H-imidazol-2-ylmethyl)-1-methanesulfonyl-4-methoxy-1H-indole; and 3-(4,5-Dihydro-1H-imidazol-2-ylmethyl)-1-methanesulfonyl-5-methoxy-4-methyl-1H-ndole.

Using a similar procedure to that described above, but replacing methanesulfonyl chloride in step 6 with the appropriate alkylsulfonyl chloride, the following were prepared:

4-Chloro-3-(4,5-dihydro-1H-imidazol-2-ylmethyl)-1-ethanesulfonyl-1H-indole;

4-Chloro-3-(4,5-dihydro-1H-imidazol-2-ylmethyl)-1-(propane-2-sulfonyl)-1H-indole.

Example 2

4-Chloro-3-(4,5-dihydro-1H-imidazol-2-ylmethyl)-1-methanesulfonyl-2-methyl-1H-indole The synthetic procedures described in this Example were carried out according to the process shown in Scheme H.

SCHEME H

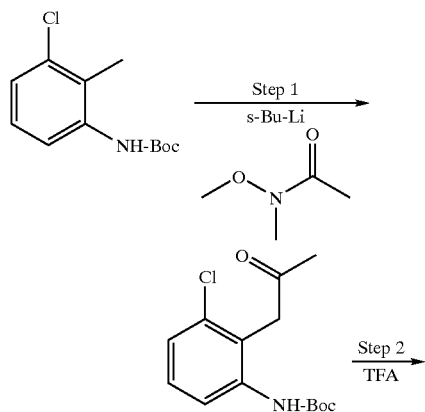

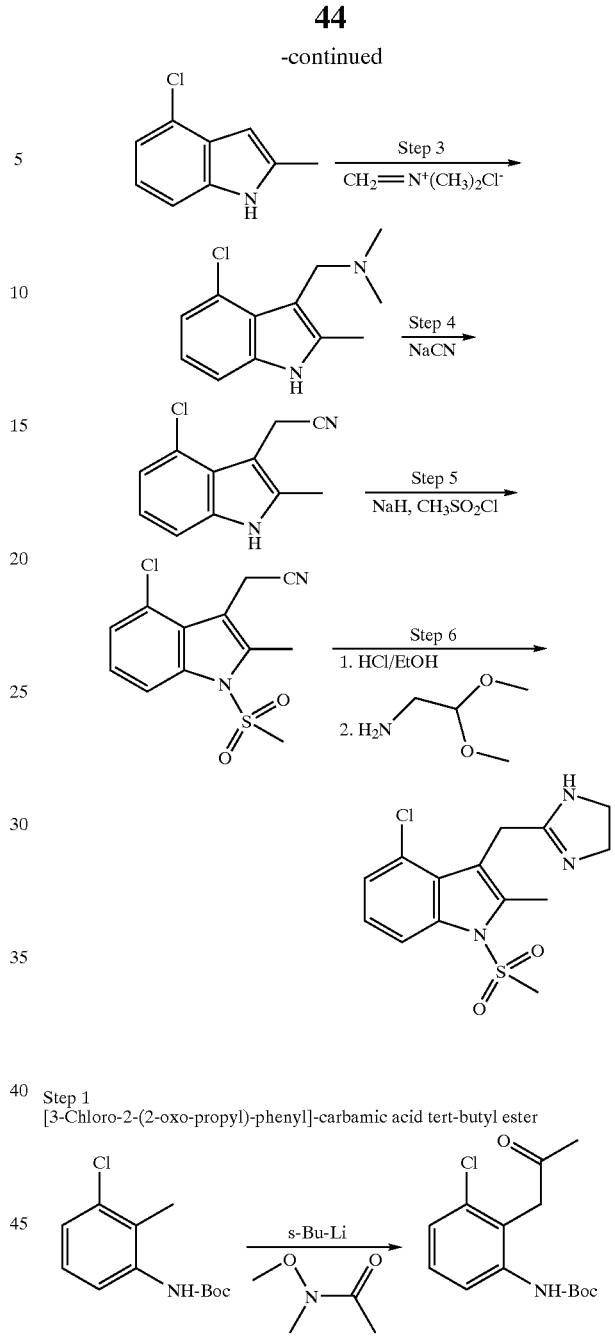

Step 1
[3-Chloro-2-(2-oxo-propyl)-phenyl]-carbamic acid tert-butyl ester

To a cold solution of (3-Chloro-2-methyl-phenyl)-carbamic acid tert-butyl ester (5.0 g, 20.7 mmol) in anhydrous tetrahydrofuran (100 ml) at −40° C. under $N_2$, was added a solution of s-butyl lithium (40 ml, 52 mmol, 1.3 M in cyclohexane) dropwise and maintained the reaction temperature below −30° C. To the bright yellow solution at −50° C. was added a solution of N-methoxy N-methylacetamide (2.33 g, 22.6 mmol) in anhydrous tetrahydrofuran (40 ml) dropwise and maintained the reaction temperature between −50° C. to −40° C. The mixture was allowed to warm to −10° C. over a period of 35 minutes and was then partitioned between diethyl ether and 0.3 N hydrochloric acid solution. The organic extract was washed with water and brine, dried (anhydrous sodium sulfate), and concentrated under reduced pressure. The residue was purified by flash column chromatography over silica gel eluting with 20% ethyl acetate in hexane to give crude [3-Chloro-2-(2-oxo-propyl)-phenyl]-carbamic acid tert-butyl ester (5.21 g) as a colorless oil.

Step 2
4-Chloro-2-methyl-1H-indole

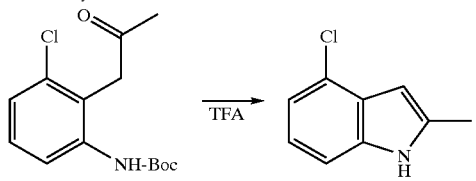

To a solution of the crude [3-Chloro-2-(2-oxo-propyl)-phenyl]-carbamic acid tert-butyl ester (5.21 g) in dichloromethane (180 ml) was added trifluoroacetic acid (20 ml). The reaction mixture was stirred at room temperature for 5 days and then partitioned between dichloromethane and 5% sodium bicarbonate solution. The organic extract was washed with brine, dried (anhydrous sodium sulfate), and concentrated under reduced pressure to give 4-Chloro-2-methyl-1H-indole and 3-Chloro-2-methyl-phenylamine as a mixture (2.6 g mixture, 69% yield of 4-Chloro-2-methyl-1H-indole). $^1$H NMR (CDCl$_3$) d: 2.45 (s, 3H), 6.32–6.33 (m, 1H), 6.98–7.18 (m, 3H), 7.96 (bs, 1H), M–H: 164.

Steps 3–5

Steps 3–5 were carried out as described above for Steps 4–6 of Example 1, to yield 4-chloro-1-methanesulfonyl-1H-indol-3-yl)-acetonitrile (1.156 g, 4.30 mmol).

Step 6
give 4-Chloro-3-(1H-imidazol-2-ylmethyl)-1-methanesulfonyl-1H-indole

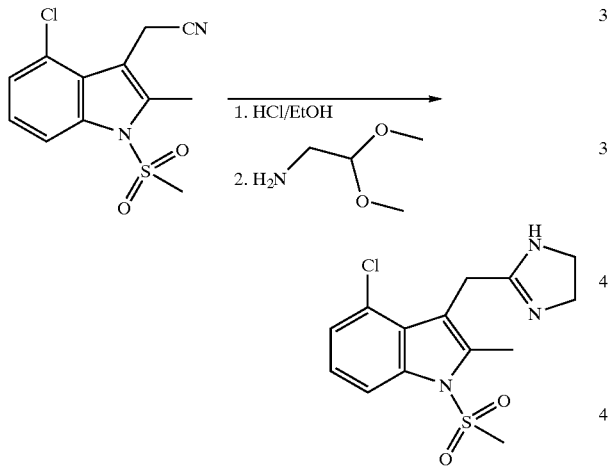

Hydrogen chloride gas was bubbled to a cold (0° C.) suspension of 4-chloro-1-methanesulfonyl-1H-indol-3-yl)-acetonitrile (1.156 g, 4.30 mmol) in absolute ethanol (50 ml) for 15 minutes. The reaction mixture was kept in refrigerator for 3.5 days. Solvent was removed under reduced pressure. The solid residue was resuspended in dry ethylene glycol dimethyl ether (20 ml). To this mixture was added aminoacetaldehyde dimethyl acetal (0.52 ml, 1.07 mmole) at 0° C. dropwise. After stirring vigorously at room temperature overnight, glacial acetic acid (99.5%, 40 ml) was added and followed by bubbling hydrogen chloride gas through the resulting mixture for 2 minutes. The mixture was heated at 50° C. for 24 hours, cooled to room temperature and poured into ether. The insoluble residue obtained after decanting the supernatant was washed with ether and redissolved in a solution of concentrated ammonium hydroxide (0.5 ml) in methanol (50 ml). Solvent was then removed under reduced pressure. The residue was purified by flash column chromatography over silica gel eluting with 3 to 5% methanol in methylene chloride with 0.1% concentrated ammonium hydroxide to give 4-Chloro-3-(1H-imidazol-2-ylmethyl)-1-methanesulfonyl-1H-indole as a cream solid (0.55 g, 41%).
$^1$H NMR (DMSO) δ: 3.46 (s, 3H), 4.34 (d, 2H, J=1.0 Hz), 6.84 (bs, 1H), 7.02 (bs, 1H) 7.32–7.45 (m, 3H), 7.84 (dd, 1H, J=7.8 Hz, 1.4 Hz), 11.73 (bs, 1H). M+H: 310.

Example 3

4-Chloro-3-(4,5-dihydro-1H-imidazol-2-ylmethyl)-1-methanesulfonyl-6-methoxy-1H-indole The synthetic procedures of this Example were carried out according to the process shown in Scheme I.

SCHEME I

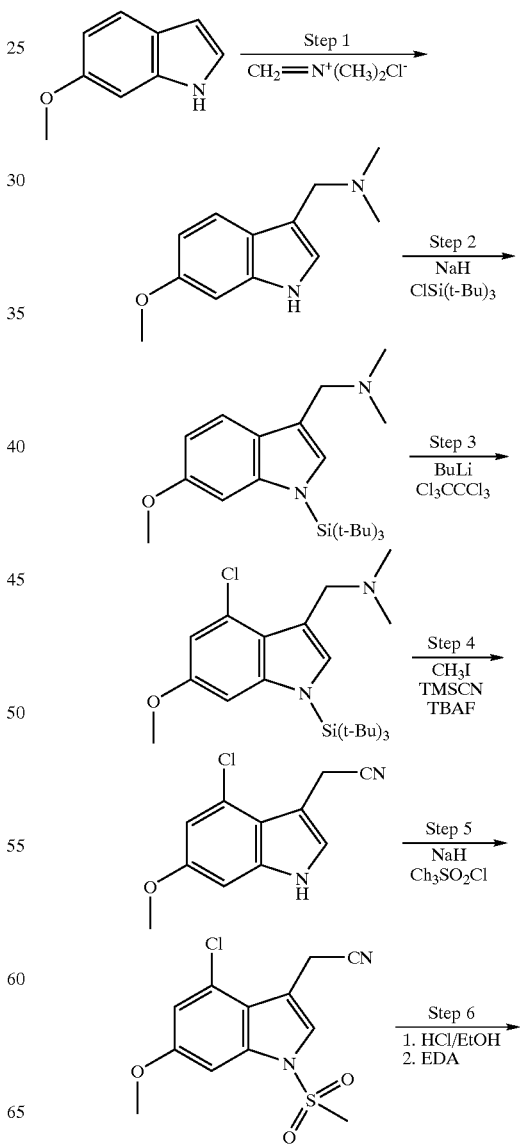

-continued

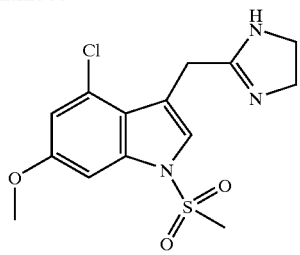

Step 1
(6-methoxy-1H-indol-3-ylmethyl)-dimethylamine

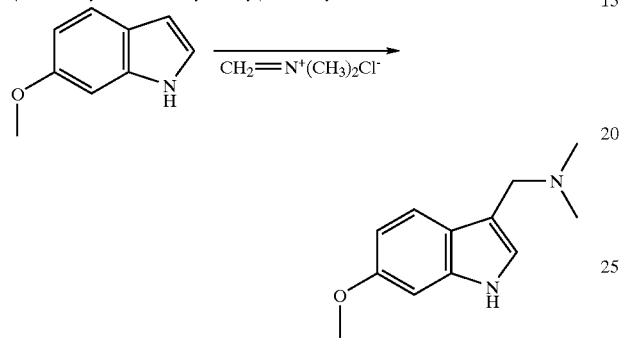

Step 1 of scheme F was carried out as described above in step 1 of Example 1 using 6-methoxy-1H-indole (Aldrich Chemical Co. Cat. No. 13,985-8), to provide (6-methoxy-1H-indol-3-ylmethyl)-dimethylamine, M+H=205.

Step 2
(6-Methoxy-tri-tert-butylsilanyl-1H-indol-3-ylmethyl)-dimethylamine

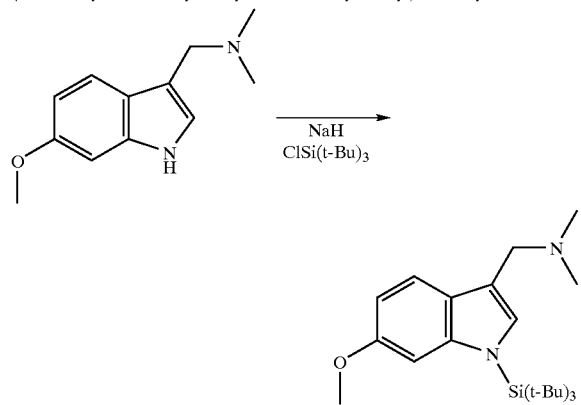

Step 2 was carried out according to the procedure described by Masatomo Iwao, Dsamu Motoi, Tsutomu Fukuda and Fumito Ishibashi; *Tetrahedron*, 54, 1998, 8999.

To a solution of (6-Methoxy-1H-indol-3-ylmethyl)-dimethyl-amine (0.076 g, 3.73 mmol) in anhydrous tetrahydrofuran (10 ml), was added sodium hydride (0.22 g, 5.59 mmol, 60% in mineral oil) at 0° C. After stirring for 10 minutes, triisopropylsilyl chloride (0.82 g, 4.10 mmol) was added dropwise over 20 min. The reaction mixture was stored at 0° C. for 16 hours and then quenched with water. The aqueous solution was extracted into ether. The ether extract was washed with brine, dried (anhydrous sodium sulfate) and concentrated under reduced pressure. The residue was triturated with hexanes and the insoluble material was removed by filtration. The filtrate was concentrated under reduced pressure to give (6-Methoxy-1-tri-tert-butylsilanyl-1H-indol-3-ylmethyl)-dimethylamine as an oil (0.76 g, 56.7%). $^1$H NMR (CDCl$_3$) δ: 1.13 (d, 18H, J=7.52 Hz), 1.67 (m, 3H), 2.25 (s, 6H), 3.57 (s, 2H), 3.83 (s, 3H), 6.80 (dd, 1H, J=2.2 Hz, 6.4 Hz), 6.99 (d, 1H, J=2.2 Hz), 7.02(s, 1H), 7.52 (d, 1H, J=6.4 Hz).

Step 3
(4-Chloro-6-methoxy-1-tri-tert-butylsilanyl-1H-indol-3-ylmethyl)-dimethylamine

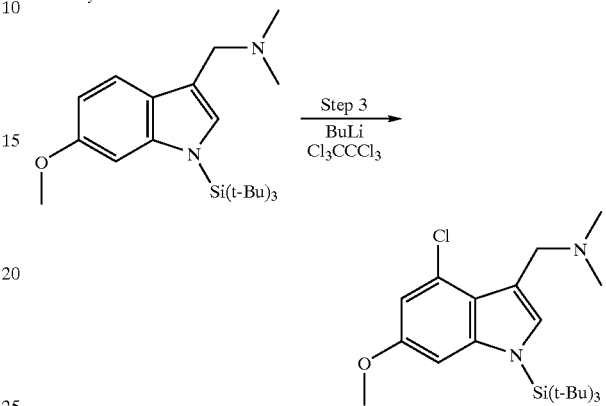

To a stirred solution of (6-methoxy-1-tri-tert-butylsilanyl-1H-indol-3-ylmethyl)-dimethylamine (0.2 g, 0.56 mmol) in anhydrous ether (20 ml) at −78° C. was added tert-butyllithium (43 mg, 0.67 mmol, 1.7M in pentane) dropwise. After being stirred for 20 min, the mixture was allowed to warm to 0° C. and was stirred for one hour. The mixture was then re-cooled to −78° C., and a solution of hexachloroethane (0.2 g, 0.84 mmol) in anhydrous ether (10 ml) was added over 10 min. The reaction mixture was warmed to room temperature and stirring was continued for another 1.5 hour before quenching with saturated ammonium chloride solution. After extracting into ether, the ether extract was dried (anhydrous sodium sulfate), and concentrated under reduced pressure to give (4-Chloro-6-methoxy-1-tri-tert-butylsilanyl-1H-indol-3-ylmethyl)-dimethylamine as an oil (0.217 g, 98.6%). $^1$H NMR (CDCl$_3$) δ:1.12 (d, 18H, J=7.52 Hz), 1.66 (m, 3H), 2.30 (s, 6H), 3.75 (s, 2H), 3.80 (s, 3H), 6.78 (d, 1H, J=2.2 Hz), 6.88 (d, 1H, J=2.2 Hz), 7.02 (s, 1H).

Step 4
(4-Chloro-6-methoxy-1H-indol-3-yl)-acetonitrile

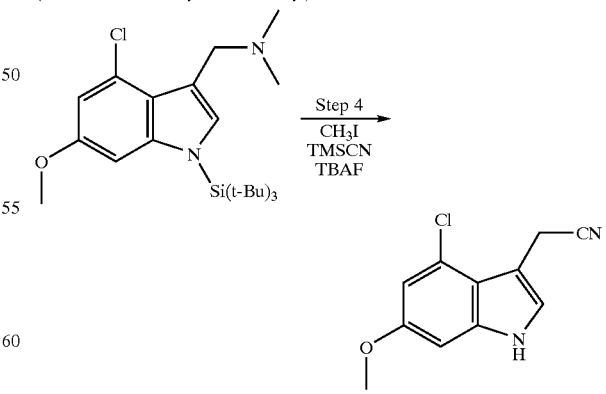

To a solution of (4-Chloro-6-methoxy-1-tri-tert-butylsilanyl-1H-indol-3-ylmethyl)-dimethyl-amine (0.73 g, 1.85 mmol) in benzene (20 ml) was added methyl iodide (0.52 g, 3.71 mmol). After stirring at ambient temperature for 16 hours, the solvent was removed under reduced pressure. The residue was suspended in anhydrous tetrahydrofuran (10 ml). To this solution was added, sequentially, trimethylsilyl cyanide (0.27 g, 2.78 mmol) and tetrabutylammonium fluoride (1.45 g, 5.56 mmol, 1M in tetrahydrofuran, after which the solution was stirred for an hour. After solvent was removed under reduced pressure, the residue was partitioned between water and ether. The ether extract was dried (anhydrous sodium sulfate) and concentrated under reduced pressure to give (4-Chloro-6-methoxy-1H-indol-3-yl)-acetonitrile as solid (0.41 g, quantitative). $^1$H NMR (CDCl$_3$) δ: 3.82 (s, 3H), 4.10 (d, 2H, J+1.17 Hz), 6.79 (d, 1H, J=2.07 Hz), 6.79 (d, 1H, J=2.07), 7.16 (m, 1H), 8.11 (b, 1H).

Step 5
(4-Chloro-1-methanesulfonyl-6-methoxy-1H-indol-3-yl)-acetonitrile

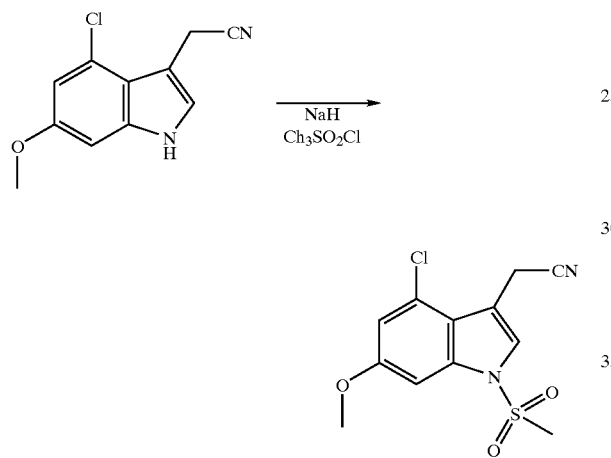

Step 5 was carried out as described in step 6 of Example 1 to provide (4-Chloro-1-methanesulfonyl-6-methoxy-1H-indol-3-yl)-acetonitrile, M+H=298.

Step 6

4-Chloro-3-(4,5-dihydro-1H-imidazol-2-ylmethyl)-1-methanesulfonyl-6-methoxy-1H-indole Step 6 was carried out as described in step 7 of Example 1 to provide 4-Chloro-3-(4,5-dihydro-1H-imidazol-2-ylmethyl)-1-methancsulfonyl-6-methoxy-1H-indole, M+H= 342.

Also prepared in the manner described above in Example 3 were the following compounds:

4-Chloro-3-(4,5-dihydro-1H-imidazol-2-ylmethyl)-6-fluoro-1-methanesulfonyl-1H-indole; and 4-Chloro-3-(4,5-dihydro-1H-imidazol-2-ylhethyl)-5-fluoro-1-methanesulfonyl-1H-indole.

Example 4

3-(4,5-dihydro-1H-imidazol-2-ylmethyl)-1-methanesulfonyl-5-methoxy-2-methyl-1H-indole The synthetic procedures of this Example were carried out according to the process shown in Scheme J.

SCHEME J

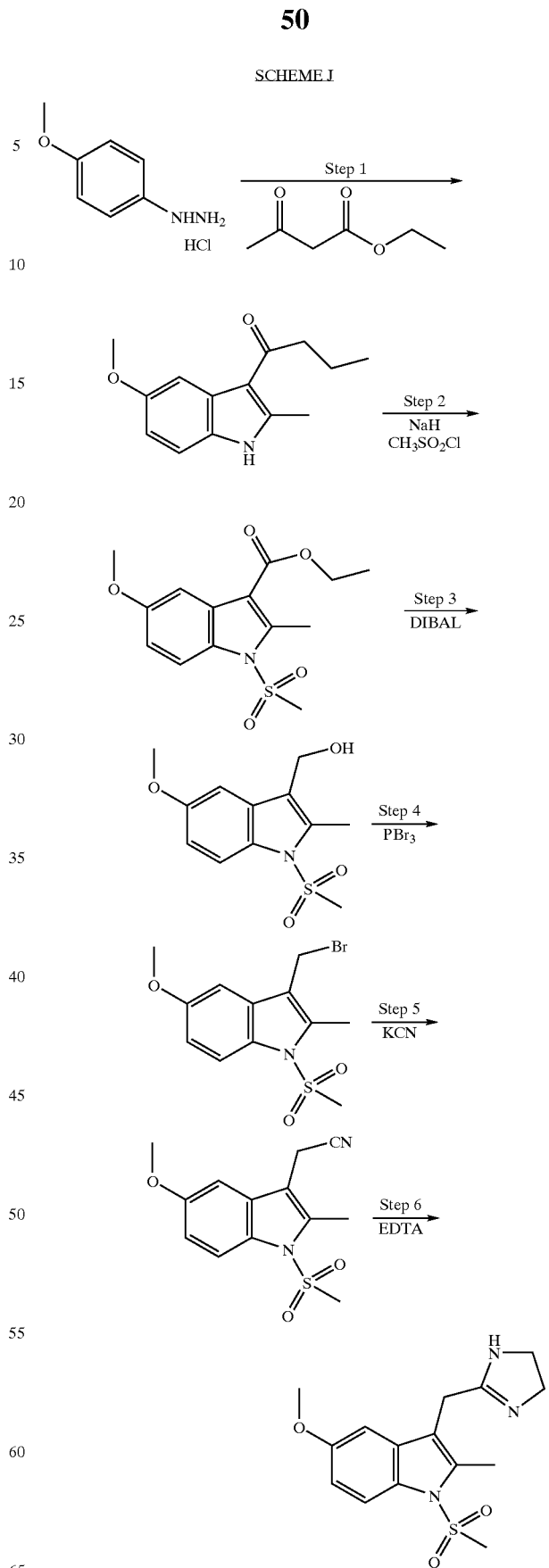

Step 1
5-Methoxy-2-methyl-1H-indole-3-carboxylic acid ethyl ester

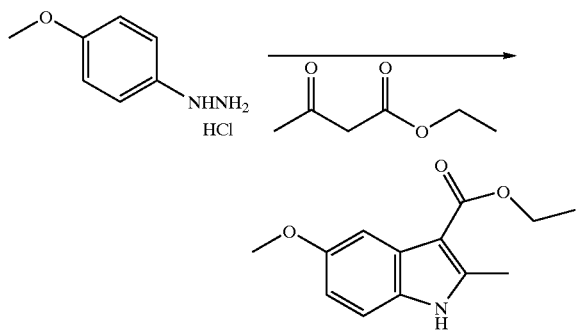

Step 3
(1-Methanesulfonyl-5-methoxy-2-methyl-1H-indole-3-yl)-methanol

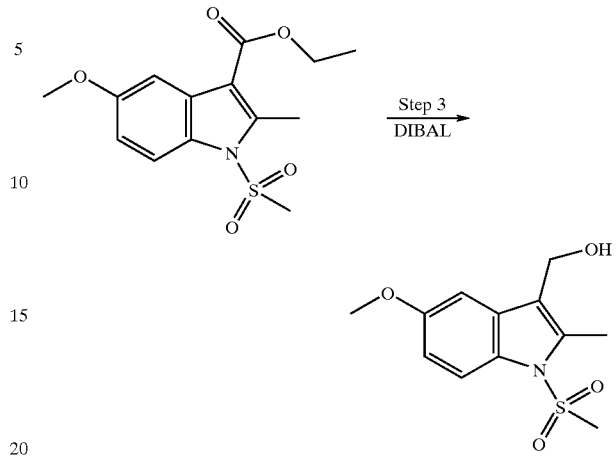

Ethyl acetoacetate (5.5 ml, 43.15 mmol) was added into a solution of (4-methoxy-phenyl)-hydrazine (5.0 g, 28.63 mmol) in glacial acetic acid (500 ml) at room temperature. The mixture was heated at 110° C. for 2 hours, and kept at room temperature for 16 hours. The mixture was concentrated under reduced pressure and the residue was partitioned between dichloromethane and 1 N sodium hydroxide solution. The organic extract was dried (anhydrous sodium sulfate) and concentrated under reduced pressure. The residue was purified by flash column chromatography over silica gel eluting with 2% methanol in dichloromethane to give 5-Methoxy-2-methyl-1H-indole-3-carboxylic acid ethyl ester as a dark solid, (3.18 g, 47%). $^1$H NMR (CDCl$_3$) δ:1.44 (t, 3H, J=7.1 Hz), 2.70 (s, 3H), 3.87 (s, 1H), 4.39 (q, 2H, J=7.1 Hz), 6.82(dd, 1H, J=8.8 Hz, 2.5 Hz), 7.17 (d, 1H, J=8.8 Hz), 7.63 d, 1H, J=2.5 Hz), 8.38 (bs, 1H). M−H: 232.

Step 2
1-Methanesulfonyl-5-methoxy-2-methyl-1H-indole-3-carboxylic acid ethyl ester

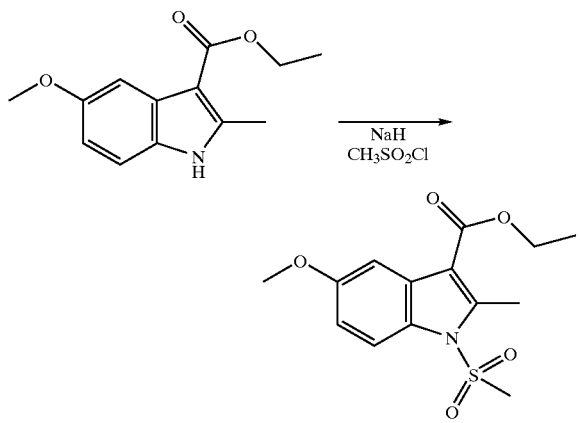

Step 2 of this Example was carried out according to the procedure described in Step 6 of Scheme 1, to provide 1-methanesulfonyl-5-methoxy-2-methyl-1H-indole-3-carboxylic acid ethyl ester, M+H=312.

Diisobutylaluminum hydride (6 ml, 6 mmol, 1M in dichloromethane) was added slowly at −78° C. under N$_2$ to a solution of 1-methanesulfonyl-5-methoxy-2-methyl-1H-indole-3-carboxylic acid ethyl ester (0.4 g, 1.29 mmol) in anhydrous tetrahydrofuran (10 ml). The reaction mixture was stirred at −78° C. for 1.5 hours and then kept at 4° C. for 16 hours. The reaction was quenched with water and stirred for 0.5 hour. The insoluble material was removed by filtration. The filtrate was concentrated under reduced pressure, and the residue was purified by flash column chromatography over silica gel eluting with 50 to 70% ethyl acetate in hexane to give (1-methanesulfonyl-5-methoxy-2-methyl-1H-indol-3-yl)-methanol as a white solid, (0.26 g, 75.2%). $^1$H NMR (CDCl$_3$) δ: 2.59 (s, 3H), 3.00 (s, 3H), 3.87 (s, 3H), 4.79 (bs, 2H), 6.91 (dd, 1H, J=9.1 Hz, 2.6 Hz), 7.11 (d, 1H, J=2.6 Hz), 7.89 (dd, 1H, J=9.1 Hz, 0.3 Hz).

Step 4
3-Bromomethyl-1-methane sulfonyl-5-methoxy-2-methyl-1H-indole

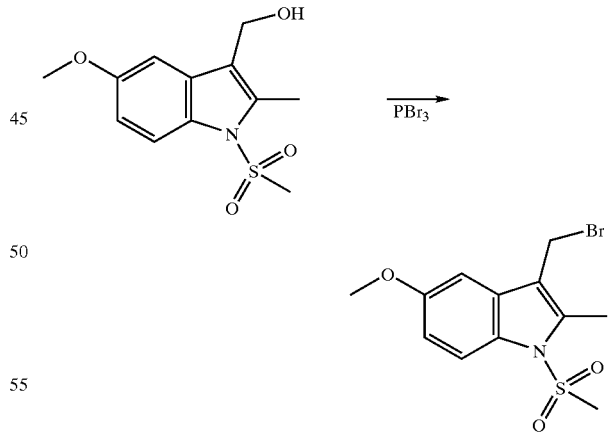

To a solution of (1-Methanesulfonyl-5-methoxy-2-methyl-1H-indol-3-yl)-methanol (1.53 g, 5.68 mmol) in anhydrous ethyl ether (50 ml) and tetrahydrofuran (20 ml) at 0° C. under N$_2$ was added a solution of phosphorus tribromide (7.5 ml, 1 M in dichloromethane). The mixture was stirred at room temperature for 8 hours and concentrated under reduced pressure to give 3-bromomethyl-1-methane sulfonyl-5-methoxy-2-methyl-1H-indole as white solid. $^1$H NMR (CDCl$_3$) δ:2.57 (s, 3H), 3.04(s, 3H), 3.89 (s, 3H), 4.63

(s, 2H), 6.93 (dd, 1H, J=9.1 Hz, 2.5 Hz), 7.04 (d, 1H, J=2.5 Hz), 7.89 (d, 1H, J=9.1 Hz).

Step 5
(1-Methanesulfonyl-5-methoxy-2-methyl-1H-indol-3-yl)-acetonitrile

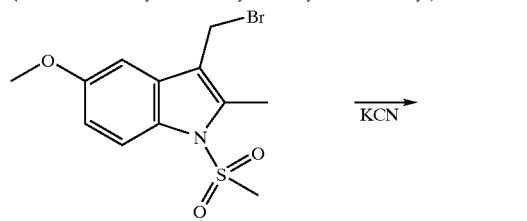

To a suspension of potassium cyanide (3.0 g, 46.1 mmol) in methyl sulfoxide (16 ml) and tetrahydrofuran (4 ml) at 0° C. was added a solution of (1-methanesulfonyl-5-methoxy-2-methyl-1H-indol-3-yl)-methanol (0.26 g,) in tetrahydrofuran (20 ml) at 0° C. The reaction mixture was stirred at room temperature for 8 hours and then kept at 4° C. for 72 hours. The mixture was partitioned between ethyl acetate and water, and the organic extract was washed with brine, dried (anhydrous sodium sulfate) and concentrated under reduced pressure. The residue was purified by flash column chromatography over silica gel eluting with 50 to 70% ethyl acetate in hexane) to give (1-methanesulfonyl-5-methoxy-2-methyl-1H-indol-3-yl)-acetonitrile as a white solid, (0.2 g, 13% in 2 steps). $^{1}$H NMR (CDCl$_{3}$) δ: 2.58 (s, 3H), 3.03 (s, 3H), 3.71 (s, 2H), 3.88 (s, 3H), 6.93–6.99 (m, 2H), 7.91 (dd, 1H, J=8.9 Hz, 0.6 Hz).

Step 6
3-(4,5-dihydro-1H-imidazol-2-ylmethyl)-1-methanesulfonyl-5-methoxy-2-methyl-1H-indol

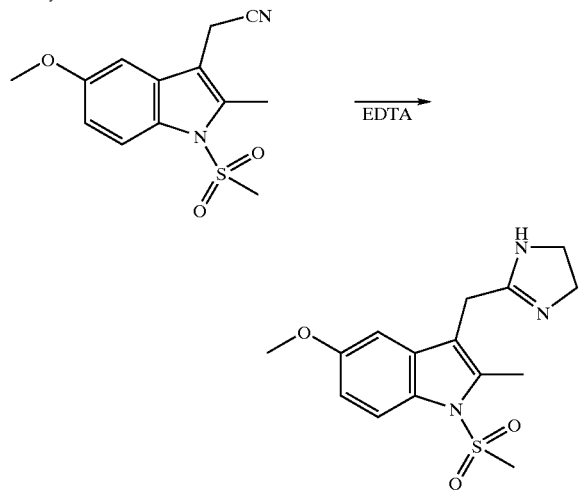

Step 6 of this Example was carried out according to the procedure described in Step 7 of Scheme 1, to provide 3-(4,5-dihydro-1H-imidazol-2-ylmethyl)-1-methanesulfonyl-5-methoxy-2-methyl-1H-indole, M+H= 312.

Also prepared by the procedure of Example 4 was:
3-(4,5-Dihydro-1H-imidazol-2-ylmethyl)-1-methanesulfonyl-1H-indole.

Example 5

4-Chloro-3-(4,5-dihydro-1H-imidazol-2-ylmethyl)-indole-1-carboxylic acid dimethylamide The synthetic procedures of this Example are shown in Scheme K.

SCHEME K

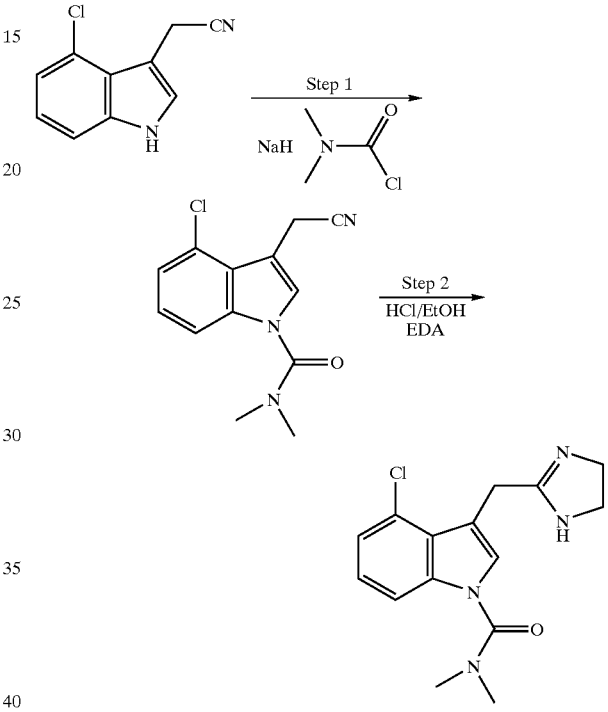

Step 1
4-Chloro-3-cyanomethyl-indole-1-carboxylic acid dimethylamide

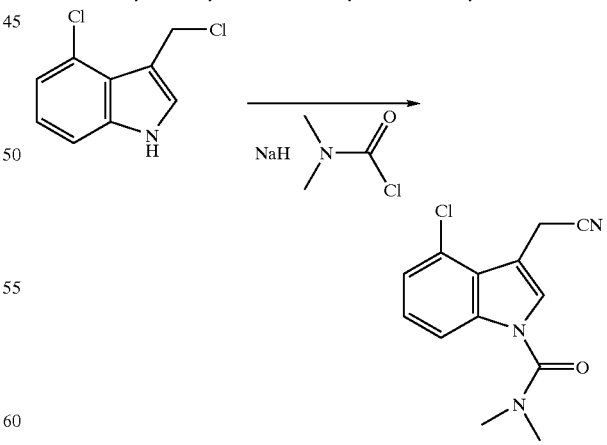

The (4-Chloro-1H-indol-3-yl)-acetonitrile used in step 1 was prepared from commercially obtained 4-chloro-1H-indole (Aldrich Chemical Co. Cat. No. 24,622-0) using the procedure of steps 4 and 5 of Example 1. The indole N-acylation in step 1 was carried out according to the procedure described by Curtin and Davidsen; J. Med. Chem.; 41; 1; 1998; 74–95.

To a solution of (4-chloro-1H-indol-3-yl)-acetonitrile (200 mg, 1.05 mmol) dissolved in anhydrous tetrahydrofuran (5 ml) at 0° C. was added sodium hydride (63 mg, 1.57 mmol, 60% dispersion in mineral oil). After 20 minutes at 0° C., the ice bath was removed and dimethyl carbamyl chloride (0.12 mL, 1.26 mmol) was slowly added. After one hour, the reaction was partitioned between ethyl acetate (100 mL) and saturated sodium chloride solution (2.5 mL). The ethyl acetate extract was dried (anhydrous magnesium sulfate), filtered and concentrated under reduced pressure. The resulting material was purified by flash column chromatography over silica gel eluting with 40% ethyl acetate in hexane to give 4-Chloro-3-cyanomethyl-indole-1-carboxylic acid dimethylamide as a white solid (239 mg, 87%).

$^1$H NMR (CDCl$_3$) δ: 3.10 (s, 6H), 4.16 (br s, 2H), 7.22 (m, 2H), 7.42 (br s, 1H), 7.57 (m, 1H); M+H 262.

Step 2
4-Chloro-3-(4,5-dihydro-1-H-imidazol-2-ylmethyl)-indole-1-carboxylic acid dimethylamide

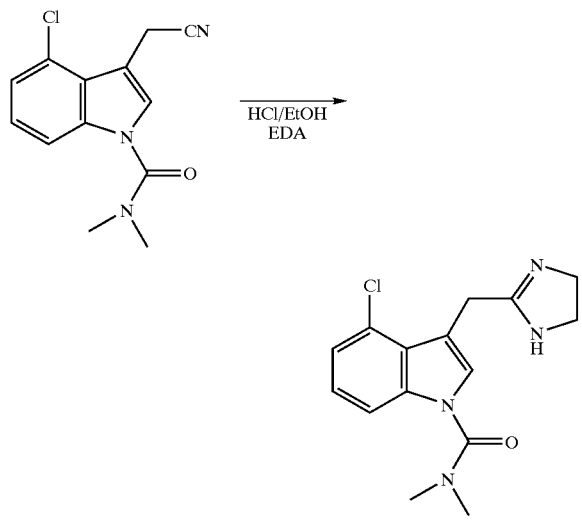

4-Chloro-3-(4,5-dihydro-1-H-imidazol-2-ylmethyl)-indole-1-carboxylic acid dimethylamide was prepared in this step by treatment of the nitrile compound of step 1 with HCl followed by ethylene diamine using the procedure of step 7 of Example 1. $^1$H NMR (DMSO-d6) δ: 3.05 (s, 6H), 3.83 (s, 4H), 4.19 (s, 2H), 7.26 (m, 2H), 7.63 (m, 1H), 7.76 (s, 1H), 9.91 (s, 2H) M+H 305.

Example 6

4-Chloro-3-(4,5-dihydro-1H-imidazol-2-ylmethyl)-indole-1-carboxylic acid methylamide The synthetic procedures of this Example are shown in Scheme L.

SCHEME L

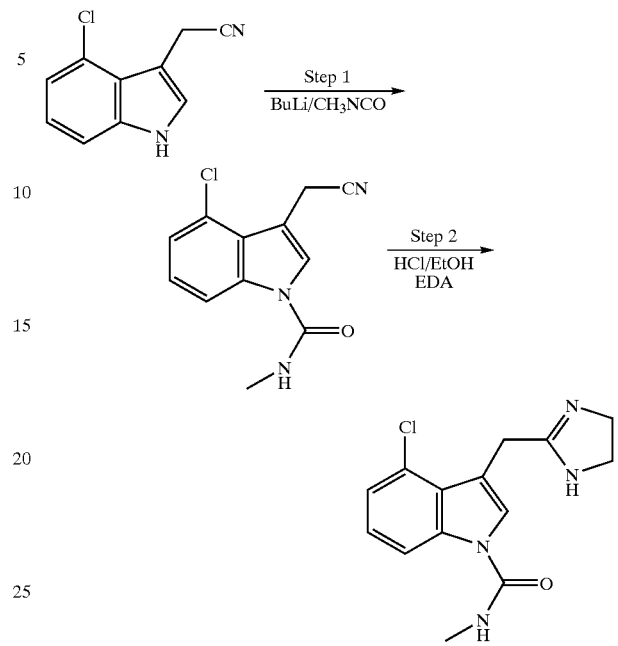

Step 1
4-Chloro-3-cyanomethyl-indole-1-carboxylic acid dimethylamide

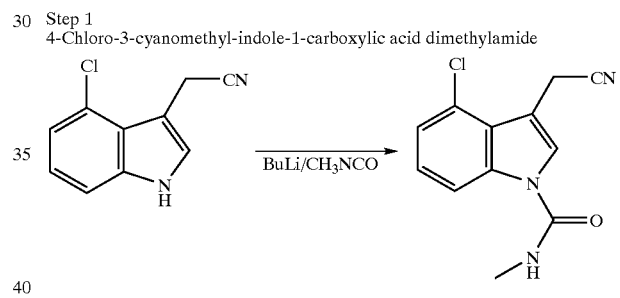

The (4-chloro-1H-indol-3-yl)-acetonitrile used in step 1 was prepared from commercially obtained 4-chloro-1H-indole (Aldrich Chemical Co. Cat. No. 24,622-0) using the procedure of steps 4 and 5 of Example 1. The indole N-acylation in step 1 was carried out according to the procedure described by Sheppard and Pireh; J. Med. Chem.; 37; 13; 1994; 2011–2032.

To a solution of 2,2,6,6-tetramethyl piperidine (0.18 ml, 1.05 mmol) dissolved in anhydrous tetrahydrofuran (5 ml) was added butyllithium (2.5M in hexanes; 0.42 ml, 1.05 mmol). The reaction was cooled to −78° C. and a solution of (4-chloro-1H-indol-3-yl)-acetonitrile (200 mg, 1.05 mmol) in anhydrous tetrahydrofuran (5 ml) was added, maintaining the temperature between −78° C. and −72° C. After 5 minutes, methyl isocyanate (0.06 ml, 1.05 mmol) was added. The dry ice bath was removed after 15 minutes and the reaction was allowed to stir overnight. After the solvent was removed under reduced pressure, the residue was partitioned between dichloromethane(100 ml) and saturated sodium chloride solution (5 ml). The organic extract was dried (anhydrous magnesium sulfate), filtered and concentrated under reduced pressure. Purification by flash column chromatography over silica gel eluting with 30% ethyl acetate in hexane to give 4-chloro-3-cyanomethyl-indole-1-carboxylic acid methylamide as a white solid (54 mg, 21%).

$^1$H NMR (CDCl$_3$) δ: 3.07 (d, 3H, J=4.7 Hz), 4.17 (s, 2H), 7.24 (m, 2H), 7.50 (s, 1H), 8.14 (m, 1H) M+247.

Step 2
4-Chloro-3-(4,5-dihydro-1-H-imidazol-2-ylmethyl)-indole-1-carboxylic acid dimethylamide

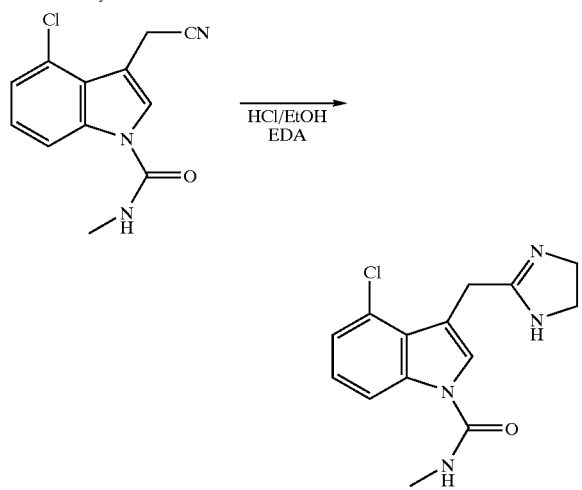

4-Chloro-3-(4,5-dihydro-1-H-imidazol-2-ylmethyl)-indole-1-carboxylic acid methylamide was obtained from the nitrile compound of step 1 using the procedure of step 7 of Example 1. $^1$H NMR (DMSO-d6) δ: 2.84 (d, 3H, J=4.3 Hz), 3.84 (s, 4H), 4.18 (br s, 2H), 7.28 (m, 2H), 7.99 (s, 1H), 8.26 (m, 1H), 8.41 (br, 1H), 9.88 (s, 2H); M+H 291.

Example 7

4-Chloro-3-(4,5-dihydro-1H-imidazol-2-ylmethyl)-indole-1-carboxylic acid amide

The synthetic procedures of this Example are shown in Scheme M.

SCHEME M

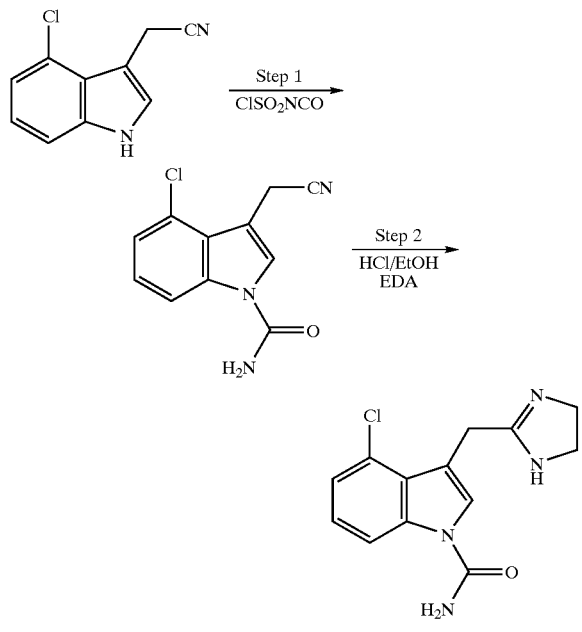

Step 1
4-Chloro-3-cyanomethyl-indole-1-carboxylic acid amide

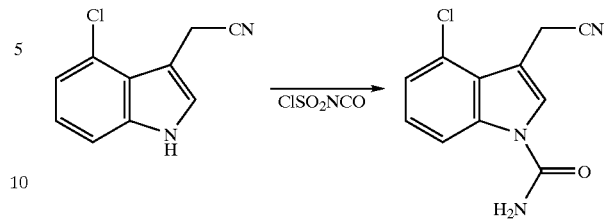

The (4-chloro-1H-indol-3-yl)-acetonitrile used in step 1 was prepared from commercially obtained 4-chloro-1H-indole (Aldrich Chemical Co. Cat. No. 24,622-0) using the procedure of steps 4 and 5 of Example 1. To (4-chloro-1H-indol-3-yl)-acetonitrile (500 mg, 2.62 mmol) dissolved in anhydrous dichloromethane (10 mL) was added chlorosulfonyl isocyanate (0.92 mL, 10.50 mmol). After 1.5 hours, the reaction was filtered and the resulting solid was washed with dichloromethane. The solid was then dissolved in acetone and water (2.5 mL) was added. The reaction mixture was concentrated to dryness to yield 4-Chloro-3-cyanomethyl-indole-1-carboxylic acid amide as a pale pink solid (377 mg, 62%). $^1$H NMR (DMSO-d6) δ: 4.27 (br s, 2H), 7.28 (m, 2H), 7.78 (br s, 2H), 7.98 (s, 1H), 8.28 (m, 1H); M+233.

Step 2

4-Chloro-3-(4,5-dihydro-1-H-imidazol-2-ylmethyl)-indole-1-carboxylic acid amide

4-Chloro-3-(4,5-dihydro-1-H-imidazol-2-ylmethyl)-indole-1-carboxylic acid amide was obtained from the nitrile compound of step 1 using the procedure of step 7 of Example 1. $^1$H NMR (DMSO-d6) δ: 3.05 (s, 6H), 3.83 (s, 4H), 4.19 (s, 2H), 7.26 (m, 2H), 7.63 (m, 1H), 7.76 (s, 1H), 9.91 (s, 2H); M+H 305.

Example 8

3-(2,5-Dihydro-1H-imidazol-2-ylmethyl)-1-methanesulfonyl-1H-pyrrolo[2,3-b]pyridine The synthetic procedures of this Example are shown in Scheme N.

SCHEME N

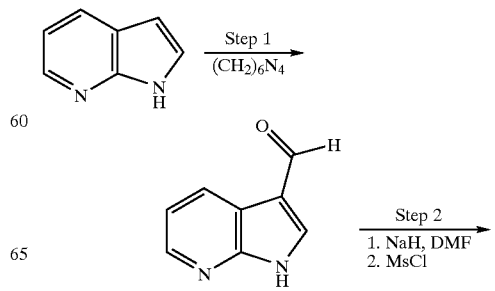

Step 2
1-Methanesulfonyl-1H-pyrrolo[2,3-b]pyridine-3-carbaldehyde

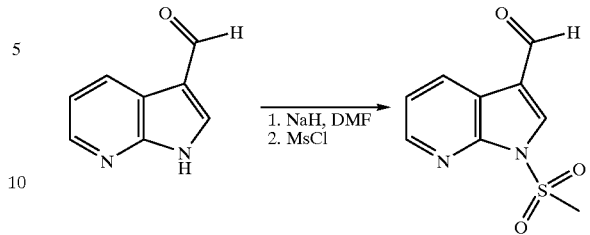

7-Azaindole-2-carboxaldehyde (2.31 g, 15.8 mmoles) from step 1 was dissolved in DMF (50 ml). Sodium hydride (0.76 g, 19 mmol) was added and the reaction was stirred at room temperature for 15 min. Methanesulfonyl chloride (1.8 ml, 24 mmoles) was added and the reaction was stirred for 3 h. The reaction mixture was diluted with ethyl acetate and washed trice with 5% lithium chloride solution, then brine. The organic layer was dried (magnesium sulfate) and concentrated to provide 1-methanesulfonyl-1H-pyrrolo[2,3-b]pyridine-3-carbaldehyde (2.84 g, 80% yield). $^1$H NMR (CDCl$_3$) δ: 3.71 (3H, s), 7.42 (1H, dd, J=4.7 Hz, 8.1 Hz), 8.30 (1H, s), 8.57 (1H, dd, J=1.7 Hz, 4.7 Hz), 8.63 (1H, dd, J=1.7 Hz, 8.1 Hz), 10.07 (s, 1H).

Step 3
1-Methanesulfonyl-1,2-dihydro-pyrrolo[2,3-b]pyridin-3-one

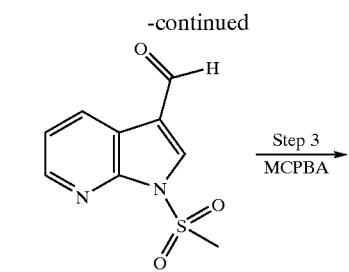

Step 3
MCPBA

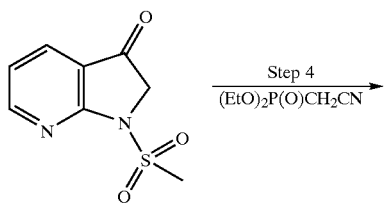

Step 4
(EtO)$_2$P(O)CH$_2$CN

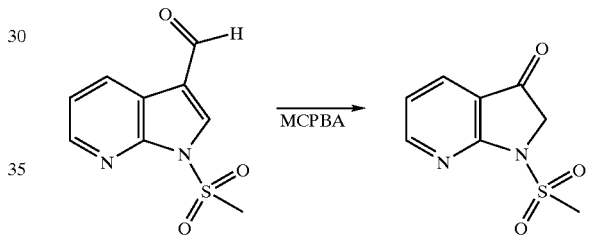

1-Methanesulfonyl-1H-pyrrolo[2,3-b]pyridine-3-carbaldehyde (2.84 g, 12.7 mmol) from step 2 was dissolved in dichloromethane (150 ml) and cooled to 0° C. Meta-chloroperbenzoic acid (3.4 g, 15 mmol) was added in several portions. The reaction mixture was stirred under a nitrogen atmosphere overnight, while slowly warming to room temperature. The reaction mixture was filtered through a plug of basic alumina and concentrated under reduced pressure to a yellow solid. The crude product was chromatographed over silica gel eluting with 50% ethyl acetate in hexane to yield 1-methanesulfonyl-1,2-dihydro-pyrrolo[2,3-b]pyridin-3-one (700 mg, 26%). $^1$H NMR (DMSO-d$_6$) δ: 3.59 (3H, s), 4.60 (2H, s), 7.45 (1H, dd, J=4.9 Hz, 7.7 Hz), 8.31 (1H, dd, J=1.8 Hz, 7.7 Hz), 8.84 (1H, dd, J=1.8 Hz, 4.9 Hz).

Step 4
(1-Methanesulfonyl-1H-pyrrolo[2,3-b]pyridin-3-yl)-acetonitrile

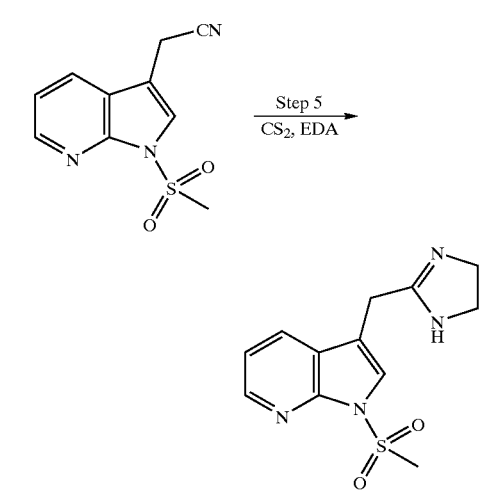

Step 5
CS$_2$, EDA

Step 1
7-Azaindole-2-carboxaldehyde

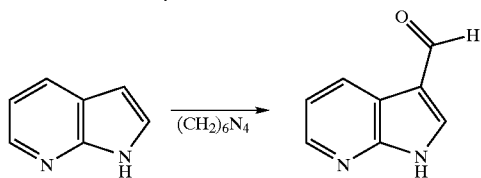

To a solution of 7-Azaindole (Aldrich Chemical Co. Cat No. A9,550-2, 4.12 g, 34.9 mmol) in 33% acetic acid (43 ml) was added Hexamethylenetetramine (7.3 g, 5.2 mmol) and the reaction was heated at reflux for 6 hours. The reaction mixture was cooled to room temperature and diluted with ice water (100 ml). The mixture was then left at 0° C. for 18 h. to crystallize product. The beige powder was filtered and washed with water to provide 7-azaindole-2-carboxaldehyde (2.95 g, 58%). $^1$H NMR (DMSO-d$_6$) δ:7.28 (1H, dd, J=4.8 Hz, 7.9 Hz), 8.37 (1H, dd, J=1.6 Hz, 4.8 Hz), 8.42 (1H, dd, J=1.6 Hz, 7.9 Hz), 8.47 (1H, s), 9.94 (s, 1H).

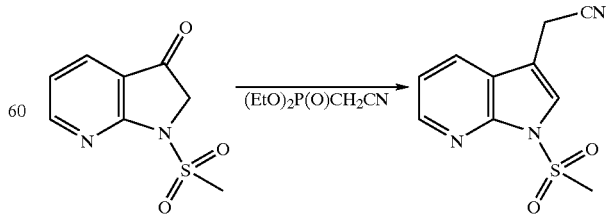

Diethyl(cyanomethyl)phosphonate (0.47 ml, 3.1 mmol) was dissolved in tetrahydrofuran (5 ml) and cooled to 0° C.

Sodium hydride (0.12 g, 3.1 mmol) was added portionwise and the reaction was stirred for 10 min. 1-Methanesulfonyl-1,2-dihydro-pyrrolo[2,3-b]pyridin-3-one (0.332 g, 1.57 mmoles) suspended in tetrahydrofuran (3 ml) was added dropwise, whereupon it immediately dissolved. The reaction was stirred at room temperature for 2 h. The reaction mixture was diluted with water and neutralized with 1M hydrochloric acid The aqueous solution was extracted with ethyl acetate. The organic extract was washed with brine, dried (sodium sulfate) and concentrated under reduced pressure. The crude product was chromatographed over silica gel eluting with 50% ethyl acetate in hexane to provide pure (1-methanesulfonyl-1H-pyrrolo[2,3-b]pyridin-3-yl)-acetonitrile (0.30 g, 45%). $^1$H NMR (CDCl$_3$) δ: 3.61 (3H, s), 3.81 (2H, s), 7.34 (1H, dd, J=4.8 Hz, 7.9 Hz), 8.02 (1H, dd, J=1.6 Hz, 7.9 Hz), 8.54 (1H, dd, J=1.6 Hz, 4.8 Hz).

Step 5
3-(2,5-Dihydro-1H-imidazol-2-ylmethyl)-1-methanesulfonyl-1H-pyrrolo[2,3-b]pyridine

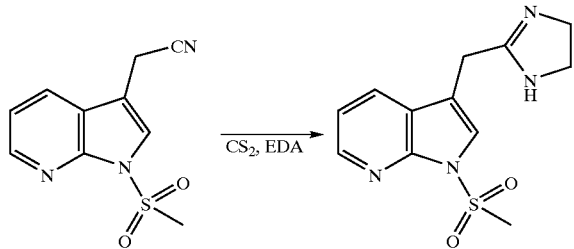

Carbon disulfide (2 drops) and (1-Methanesulfonyl-1H-pyrrolo[2,3-b]pyridin-3-yl)-acetonitrile (4) (81 mg, 0.34 mmol) was added sequentially in this order to ethylenediamine (2 ml). The reaction was heated at 140° C. for 30 minutes and concentrated under reduced pressure. The residue was chromatographed over silica gel eluting with 92:8:1 ethyl acetate:methanol:ammonium hydroxide to obtain 3-(2,5-Dihydro-1H-imidazol-2-ylmethyl)-1-methanesulfonyl-1H-pyrrolo[2,3-b]pyridine (50 mg, 53%). $^1$H NMR (DMSO-d$_6$) δ: 3.40 (4H, s), 3.70 (3H, s), 7.37 (1H, dd, J=4.7 Hz, 7.9 Hz), 7.64 (1H, s), 8.11 (1H, dd, J=1.5 Hz, 7.9 Hz), 8.42 (1H, dd, J=1.5 Hz, 4.7 Hz); M+H 279.

Example 9

A variation on the prodecure of Example 1, shown in Scheme O below, was used to prepare 4-Chloro-3-(1H-imidazol-2-ylmethyl)-1-methanesulfonyl-1H-indole.

SCHEME O

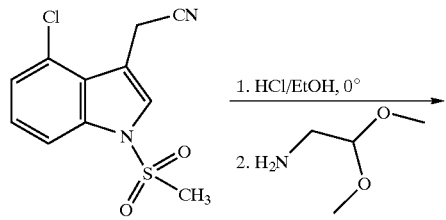

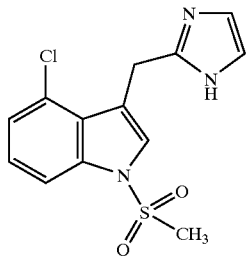

4-Chloro-3-(1H-imidazol-2-ylmethyl)-1-methanesulfonyl-1H-indole (4-Chloro-1-methanesulfonyl-1H-indol-3-yl)-acetontrile (1.156 g. 4.30 mmol) was suspended in absolute ethanol (50 mL), cooled to 0° C., and hydrogen chloride gas was bubbled therethrough for 15 minutes. The reaction mixture was then kept in refrigerator for 3.5 days, after which solvent was removed under reduced pressure. The solid residue was resuspended in dry ethylene glycol dimethyl ether (20 ml). To this mixture was added aminoacetalaldehyde dimethyl acetal (0.52 ml, 1.07 mmole) at 0° C. dropwise. After stirring vigorously at room temperature overnight, glacial acetic acid (99.5%, 40 ml) was added and followed by bubbling hydrogen chloride gas through the resulting mixture for 2 minutes. The mixture was heated at 50° C. for 24 hours, cooled to room temperature, and poured into ether. The insoluble residue obtained after decanting the supernatant was washed with ether and redissolved in a solution of concentrated ammonium hydroxide (0.5 ml) in methanol (50 ml). Solvent was then removed under reduced pressure. The residue was purified by flash column chromatography over silica gel eluting with 3 to 5% methanol in methylene chloride with 0.1% concentrated ammonium hydroxide to give 4-Chloro-3-(1H-imidazol-2-ylmethyl)-1-methanesulfonyl-1H-indole as a cream solid (0.55 g, 41%). $^1$H NMR (DMSO) δ: 3.46 (s, 3H), 4.34 (d, 2H, J=1.0 Hz), 6.84 (bs, 1H), 7.02 (bs, 1H) 7.32–7.45 (m, 3H), 7.84 (dd, 1H, J=7.8 Hz, 1.4 Hz), 11.73 (bs, 1H). M+H: 310.

Example 10

Pharmaceutical Formulations

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (IV) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 11

Functional Assay for Alpha-1A/L Agonist Activity

The inhibitory activity of compounds of this invention in vitro was examined using fluorescent dye determination of intracellular calcium concentrations.

Fluo-3 Loaded Cell Preparation:

Chinese hamster ovary cells CHO-K1 expressing the alpha-1A adrenoceptors (clone 13) are washed 4 times (approx. 300 $\mu$L/well) with fluorometric imaging plate reader (FLIPR) buffer (Hank's buffered saline solution (HBSS), 2 mM $CaCl_2$, 10 mM HEPES, 2.5 mM probenecid, 100 $\mu$M ascorbic acid), with a final volume of 150 $\mu$L/well. Cells are loaded with 50 $\mu$L/well of 8 $\mu$M Fluo-3 AM (Molecular Probes, Eugene, Oreg.), for a final concentration of 2 $\mu$M Fluo-3 AM. Cells are then incubated for 60 min at 37° C. Following dye loading, cells are washed 4 times (approx. 300 $\mu$L/well) with FLIPR buffer with a final volume of 150 $\mu$L/well.

Agonist Assay

The Test compound, control compound and reference compound are run in quadruplicate, 8-point curves on each plate with a final assay concentration range of $10^{-4}$M to $10^{-11}$M for each compound. All compounds are dissolved in DMSO at 10 mM, and serially diluted in FLIPR buffer.

The assay plate is placed in the FLIPR incubation chamber and a baseline fluorescence measurement (excitation @ 488 nm and emission @ 510–570 nm) is obtained (15 sec interval). An experimental run is then commenced. The reaction is started with the addition of 50 $\mu$L/well (at 4× final concentration) of test, control, or reference compound solution from the agonist plate to the assay plate to all 96 wells simultaneously. Fluorescence is measured for 120 sec at 1 sec intervals. Then, a second addition of 5 μM ionomycin (50 μL/well from 5× concentration ionomycin plate) is added to the assay plate. Fluorescence is measured for 30 sec at 1 sec intervals. All experiments are conducted at room temperature.

Measurements

For each assay plate, responses (increase in peak fluorescence) in each well following addition of agonist (test, control and reference) are determined. These responses may be expressed as raw CFU (Corrected Fluorescence Units), as a % maximum ionomycin response or other unit as determined by the investigator.

Statistics

For test compound, control compound (Noerepinephrine (NE) bitartrate), and reference compound, the concentration producing a 50% increase in control response ($EC_{50}$) is determined using iterative curve-fitting methods. Excel spreadsheet or Kaleidagraph software are used to fit data to the general logistic function ($E=B+E_{max} \cdot A^{nH}/A^{nH}+EC_{50}^{nH}$), where B is the corrected baseline fluorescence units (defined as zero), A is the concentration of agonist added and nH is the Hill slope (constrained to unity). $EC_{50}$ values and maxima ($E_{max}$) for each curve can be estimated objectively using this software.

In addition the intrinsic activity (α) is determined. Intrinsic activity is defined as the maximum response to test agonist divided by the maximum response to a full agonist acting through the same receptor. For these experiments, the full agonist is defined as Norepinephrine (NE) bitartrate (control).

As used herein an agonist is a compound that elicits a maximal response greater than 50% of that of norpepinephrine with a $pEC_{50}>5.5$.

The compounds prepared in the above examples are alpha-1A/L agonists.

Example 12

Assays for Alpha-1A/L Adrenoceptor Activity

Compounds used in this example were from Sigma Chemical Co., St. Louis, Mo., U.S.A.) unless specified otherwise.

In Vitro:

Male white New Zealand rabbits (3–3.5 kg) and Sprague-Dawley rats (250–400 g) were euthanized by $CO_2$ asphyxiation. The bladder (rabbit) or aorta (rat) were removed, extraneous tissue was dissected away, and tissues were placed in oxygenated Krebs' solution (mM: NaCl, 118.5; $NaHCO_3$, 25; dextrose, 5; KCl, 4.8; $CaCl_2$, 2.5; $MgSO_4$, 1.2 and $KH_2PO_4$, 1.2). Cocaine (30 μM), corticosterone (30 μM), ascorbic acid (100 μM), indomethacin (10 μM) and propranolol (1 μM) were added to the Krebs' solution to block neuronal uptake, extraneuronal uptake, auto-oxidation of catecholamines, prostanoid synthesis, beta-adrenoceptors, respectively. The alpha-2 adrenoceptor antagonist idazoxan (0.3 μM, Research Biochemicals, Inc., Natick, Mass., U.S.A.) and the calcium channel antagonist nitrendipine (1 μM, Research Biochemico International, Natick, Mass., U.S.A.) were added the Krebs' solution for rabbit and rat experiments, respectively. Strips of bladder neck (rabbit) approximately 0.8–1.2 cm in length and 2–3 mm in width and aortic rings (2–4 per rat) approximately 3 mm in width, cut as near the heart as possible, were suspended in water-jacketed tissue baths at a resting tension of 1. Tissues were maintained at 34° C. and bubbled continuously with an oxygen/carbon dioxide mixture.

Tissues were primed with norepinephrine (10 μM) and washed for 60 minutes before constructing a first cumulative concentration-effect to norepinephrine. Tissues were then washed for 60 minutes before constructing a second concentration-effect curve to a test agonist. The concentration producing the half maximal response ($pEC_{50}$) and the intrinsic activity (relative to norepinephrine) were recorded. Results for standards and representative compounds of the present invention were determined. Representative compounds of the invention showed activity in this assay.

In Vivo: Anesthetized Pig Urethra/Blood Pressure Model:

Female Yucatan micropigs (12–35 kg; ≧10 months old) were anesthetized with ketamine (Aveco Co., Ft. Dodge, Iowa, U.S.A.) followed by pentobarbital (Schering Plough Animal Health Corp., Kenilworth, N.J., U.S.A.). A cuffed endotracheal tube was placed in the trachea and the pig mechanically ventilated with room air under positive pressure. The right or left femoral artery and vein were isolated and cannulated. One of the two cannulae inserted into the femoral vein was used to infuse pentobarbital (5–20 mg/kg/hr) via an infusion pump. The second cannula was used to administer test compounds. The cannula inserted into the femoral artery was connected to a blood pressure transducer (Gould/Statham Sprectamed P23 series) for the measurement of aortic blood pressure. Needle electrodes were placed subcutaneously to record a limb lead II ECG and heart rate was monitored by a tachometer triggered by the R-wave of the ECG. Body heat was maintained with an Aquamatic hot water blanket, model K-20, and rectal temperature was continuously monitored with a YSI TeleThermometer, model 43TA.

Following a ventral midline laparotomy, both ureters were cannulated for the exteriorization of urine. The bladder was emptied and a water-filled balloon catheter (reservoir tip of a latex condom attached to PE-190 tubing) attached to an external pressure transducer was inserted through the bladder via a stab incision. The balloon catheter was advanced into the urethra and secured with silk ligatures. Correct placement of the balloon was verified by palpating the urethra when inflating and deflating the balloon.

Following the surgical preparation, blood gases (analyzed by a Nova Stat Profile 3 blood gas analyzer) and pH were adjusted to within normal limits by adjusting respiratory rate, tidal volume, and/or positive-end expiratory pressure. Intraurethral pressure was adjusted to an appropriate baseline (20–40 cm $H_2O$) by inflating or deflating the balloon. Following a 30 minute stabilization period, the pig was pretreated with a beta-adrenoceptor antagonist (propranolol; 100 μg/kg, iv), a non-selective alpha-2 adrenoceptor antagonist [8aR-(8aa,12aa,13aa)]-N-[3-[(5,8a,9,10,11,12a,13,13a-octahydro-3-methoxy-6H-isoquinol[2,1-g][1,3]naphthyridin-12(8H)-yl)-sulfonyl]propyl]-methanesulfonamide (for example, prepared by procedures described by Clark et al., European Patent Application No. 524004 A1) above for compounds according to the present invention) (300 μg/kg, iv) and a ganglionic antagonist (chlorisondamine; 200 μg/kg, iv, prepared according to the procedure described in U.S. Pat. No. 3,025,294). A single phenylephrine challenge (10 μg/kg, iv) was given to verify intraurethral and blood pressure responses. After the response returned to baseline, multiple escalating doses of agonists were administered intravenously and maximal intraurethral and diastolic blood pressure responses following each dose were recorded. Intervals between doses varied from 5–120 minutes to allow responses to return to baseline before giving the next dose. At the end of each experiment, pigs were euthanized by a lethal injection of pentobarbital. The maximum responses for intraurethral and diastolic blood pressure for standards and representative compounds of the invention were determined. Representative compounds of the invention showed activity in this assay.

In Vivo: Conscious Pig Urethra/Blood Pressure Model:

Female Yucatan micropigs (12–35 kg; ≧10 months old) were trained to rest quietly in a sling for a week prior to surgery. Only those pigs which acclimated to the sling were used for the study. Pigs were surgically instrumented under aseptic conditions. A telemetry device (Data Science International, St. Paul, Minn., U.S.A., model TA11PAD-70) was implanted into the pig with the cannula potion of the device inserted into the right external iliac artery and advanced into the abdominal aorta. The transmitter portion of the device was placed in a pocket created under the skin in close proximity to the insertion point of the cannula. A vascular access port (Sims Deltec, St. Paul, Minn., U.S.A.) with a silicon catheter was implanted for intravenous administration oftest compounds. The catheter portion was inserted into the left or right jugular vein with the port under the skin in the shoulder area. A strain-gauge transducer (SF Products, Madison, Wis., U.S.A.) was sutured to the urethra and the wire exteriorized dorsally. Pigs were allowed at least one week to recover from surgery.

One each experimental day, pigs were placed in the sling and allowed to stabilize before administering a phenylephrine prime (10 μg/kg, iv) to verify the placement of the needle in the vascular access port and calibration of the telemetry and strain-gauge probes. After urethral tension and blood pressure returned to baseline values, a non-cumulative dose-response curve to phenylephrine was constructed. Intervals between doses varied form 5–120 minutes to allow blood pressure to return to baseline levels. Sixty minutes after the last phenylephrine dose returned to baseline, a second non-cumulative curve to test compound was constructed. Responses to test compounds were expressed as a percentage of the maximum response obtained with phenylephrine. Representative compounds of the invention showed activity in this assay. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula I:

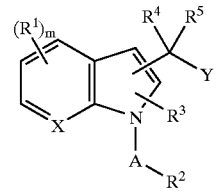

or a pharmaceutically acceptable salt or prodrug thereof, wherein:

m is from 0 to 4;

X is carbon or nitrogen;

Y is a radical of formula i, ii or iii;

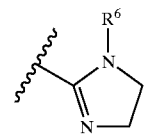

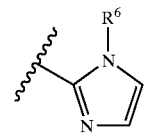

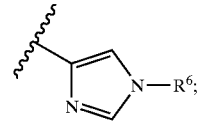

each $R^1$ independently is halogen, haloalkyl, alkyl, hydroxy, alkoxy, cyano, nitro, —S(O)$_n$R$^a$, —NR$^a$R$^b$, —NR$^a$SO$_2$R$^b$, —SO$_2$NR$^a$R$^b$, optionally substituted phenyl, optionally substituted benzyl or optionally substituted benzyloxy, where n is from 0 to 2 and R$^a$ and R$^b$ in each independent occurrence are hydrogen or alkyl;

A is —SO$_2$— or —(C=O)—;

$R^2$ is alkyl or —(CH$_2$)$_p$—NR$^c$R$^d$ where p is from 0 to 3 and R$^c$ and R$^d$ each independently is hydrogen or alkyl; and $R^3$, $R^4$, $R^5$ and $R^6$ each independently are hydrogen or alkyl.

2. The compound of claim 1, wherein $R^3$ is located at the 2-position of the indole ring system.

3. The compound of claim 2, wherein Y is of the formula i.

4. The compound of claim 3, wherein X is carbon.

5. The compound of claim 4, wherein A is —SO$_2$—.

6. The compound of claim 5, wherein $R^2$ is alkyl.

7. The compound of claim 6, wherein $R^4$ and $R^5$ are hydrogen.

8. The compound of claim 6, wherein $R^2$ is methyl, ethyl or isopropyl.

9. The compound of claim 6, wherein $R^6$ is hydrogen.

10. The compound of claim 6, wherein m is from 0 to 2, and each $R^1$ independently is halogen, alkyl or alkoxy.

11. The compound of claim 6, wherein $R^3$ is hydrogen.

12. The compound of claim 6, wherein $R^3$ is alkyl.

13. The compound of claim 4, wherein A —(C=O)—.

14. The compound of claim 13, wherein $R^2$ is —$(CH_2)_p$—$NR^cR^d$.

15. The compound of claim 14, wherein p is 0.

16. The compound of claim 15, wherein $R^c$ and $R^d$ are hydrogen.

17. The compound of claim 15, wherein $R^c$ and $R^d$ are alkyl.

18. The compound of claim 15, wherein one of $R^c$ and $R^d$ is hydrogen and the other is alkyl.

19. The compound of claim 15, wherein $R^c$ and $R^d$ are methyl.

20. The compound of claim 15, wherein one of $R^c$ and $R^d$ is hydrogen and the other is methyl.

21. The compound of claim 15, wherein $R^4$ and $R^5$ are hydrogen.

22. The compound of claim 15, wherein $R^6$ is hydrogen.

23. The compound of claim 15, wherein m is from 0 to 2, and each $R^1$ independently is halogen, alkyl or alkoxy.

24. The compound of claim 15, wherein $R^3$ is hydrogen.

25. The compound of claim 15, wherein $R^3$ is alkyl.

26. A compound of the formula II:

II:

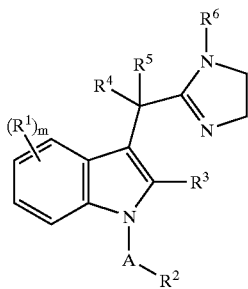

or a pharmaceutically acceptablesalt or prodrug thereof, wherein:

m is from 0 to 4;

each $R^1$ independently is halogen, haloalkyl, alkyl, hydroxy, alkoxy, cyano, nitro, —$S(O)_nR^a$, —$NR^aR^b$, —$NR^aSO_2R^b$, —$SO_2NR^aR^b$, optionally substituted phenyl, optionally substituted benzyl or optionally substituted benzyloxy, where n is from 0 to 2 and $R^a$ and $R^b$ in each independent occurrence are hydrogen or alkyl;

A is —$SO_2$— or —(C=O)—;

$R^2$ is alkyl or —$(CH_2)_p$—$NR^cR^d$ where p is from 0 to 3 and $R^c$ and $R^d$ each independently is hydrogen or alkyl; and $R^3$, $R^4$, $R^5$ and $R^6$ each independently are hydrogen or alkyl.

27. The compound of claim 26, wherein A is —$SO_2$—.

28. The compound of claim 27, wherein $R^2$ is alkyl.

29. The compound of claim 28, wherein $R^4$ and $R^5$ are hydrogen.

30. The compound of claim 29, wherein $R^2$ is methyl, ethyl or isopropyl.

31. The compound of claim 30, wherein $R^6$ is hydrogen.

32. The compound of claim 31, wherein m is from 0 to 2, and each $R^1$ independently is halogen, alkyl or alkoxy.

33. The compound of claim 32, wherein $R^3$ is hydrogen.

34. The compound of claim 26, wherein A —(C=O)—.

35. The compound of claim 34, wherein $R^2$ is —$(CH_2)_p$—$NR^cR^d$.

36. The compound of claim 35, wherein p is 0.

37. The compound of claim 36, wherein $R^4$ and $R^5$ are hydrogen.

38. The compound of claim 36, wherein $R^c$ and $R^d$ are hydrogen.

39. The compound of claim 36, wherein $R^c$ and $R^d$ are alkyl.

40. The compound of claim 36, wherein one of $R^c$ and $R^d$ is hydrogen and the other is alkyl.

41. The compound of claim 36, wherein $R^c$ and $R^d$ are methyl.

42. The compound of claim 36, wherein one of $R^c$ and $R^d$ is hydrogen and the other is methyl.

43. The compound of claim 36, wherein $R^6$ is hydrogen.

44. The compound of claim 36, wherein m is from 0 to 2, and each $R^1$ independently is halogen, alkyl or alkoxy.

45. The compound of claim 36, wherein $R^3$ is hydrogen.

46. The compound of claim 26, wherein said compound is of the formula III:

III:

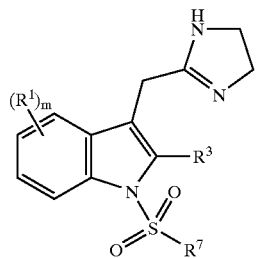

wherein $R^7$ is alkyl, and m, $R^1$, $R^2$ and $R^3$ are as defined in claim 26.

47. The compound of claim 26, wherein said compound is of the formula IV:

IV:

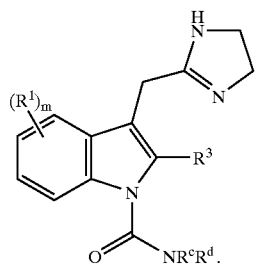

48. The compound of claim 3, wherein X is nitrogen.

49. The compound of claim 48, wherein A is —$SO_2$—.

50. The compound of claim 49, wherein $R^2$ is alkyl, and $R^4$ and $R^5$ are hydrogen.

51. A pharmaceutical composition comprising a therapeutically effective amouint of at least one compound of claim 1 together with a with a pharmaceutically acceptable carrier.

52. A method for treating a disorder modulated by alpha-1A/L adrenoceptors, wherein the disorder is selected from the group consisting of urge incontinence, stress incontinence, overflow incontinence, functional incontinence, sexual dysfunction, said method comprising administering to a subject in need thereof an effective amount of a compound of claim 1.

53. A method of treating a disease state comprising urinary incontinence, wherein the disease state is selected from the group consisting of urge incontinence, stress incontinence, overflow incontinence, functional incontinence, sexual dysfunction, by administering to a subject in need thereof an effective amount of a compound of claim 1.

54. The method of claim 52, wherein the disorder is stress incontinence.

55. The method of claim 52, wherein the disorder is urge incontinence.

56. A process for preparing a compound as claimed in claim 26, the process comprising:

reacting a compound of the formula aa:

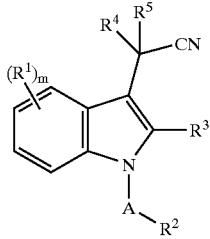

aa wherein m, $R^1$, $R^2$, $R^3$, $R^4$ and $R^5$ are as defined in claim 26, with an alkylene diamine, to form a compound of the formula II:

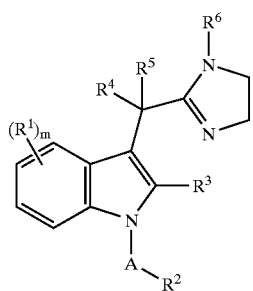

II wherein and $R^6$ is as defined in claim 26.

* * * * *